US012595447B2

(12) United States Patent
Angelescu et al.

(10) Patent No.: US 12,595,447 B2
(45) Date of Patent: Apr. 7, 2026

(54) FIELD-DEPLOYABLE MULTIPLEXED SAMPLING AND MONITORING DEVICE AND BACTERIAL CONTAMINATION MEASUREMENT METHOD

(71) Applicant: FLUIDION SAS, Paris (FR)

(72) Inventors: Dan E. Angelescu, Le Perreux sur Marne (FR); Andreas Hausot, Paris (FR)

(73) Assignee: FLUIDION SAS, Paris (FR)

( * ) Notice: Subject to any disclaimer, the term of this patent is extended or adjusted under 35 U.S.C. 154(b) by 294 days.

(21) Appl. No.: 18/189,059

(22) Filed: Mar. 23, 2023

(65) Prior Publication Data

US 2023/0227759 A1     Jul. 20, 2023

Related U.S. Application Data

(62) Division of application No. 15/909,523, filed on Mar. 1, 2018, now Pat. No. 11,618,870.

(Continued)

(51) Int. Cl.
*C12M 1/34* (2006.01)
*C12M 1/08* (2006.01)
(Continued)

(52) U.S. Cl.
CPC ................ *C12M 1/34* (2013.01); *C12M 1/08* (2013.01); *C12M 1/24* (2013.01); *C12M 1/26* (2013.01);
(Continued)

(58) Field of Classification Search
CPC . C12M 1/34; C12M 1/08; C12M 1/24; C12M 1/26; C12M 1/38; C12M 23/08;
(Continued)

(56) References Cited

U.S. PATENT DOCUMENTS 6,158,509 A    12/2000  Peterson
6,599,715 B1 *  7/2003  Vanderberg .............. C12Q 1/04
                                                              435/242

(Continued)

FOREIGN PATENT DOCUMENTS

CN          203688309 U    7/2014
DE           10023000 A1    1/2002
WO        2006116835 A1   11/2006

OTHER PUBLICATIONS

Baker et al., "To what extent can portable fluorescence spectroscopy be used in the real-time assessment of microbial water quality?" Science of the Total Environment, vol. 532, pp. 14-19 (2015), 6 pages.

(Continued)

*Primary Examiner* — Xin Y Zhong
(74) *Attorney, Agent, or Firm* — Barclay Damon LLP

(57) ABSTRACT

A system for processing samples from a body of fluid. The system includes one or more sample bottles for acquiring a sample from the body of fluid. Each sample bottle initially retains a pre-filling fluid. Each sample bottle includes a fluidic inlet port and a bottle outlet port. Each sample bottle has an inlet check valve coupled to the fluidic inlet port, the inlet check valve configured to allow fluid from the body of fluid into a sample bottle via the fluidic inlet port when the pressure difference between the body of fluid and fluid within the sample bottle reaches a threshold. The system further includes at least one pump, the bottle outlet port of each sample bottle selectively coupled to the at least one pump via a different control valve. The at least one pump is configured, in a first configuration, to remove prefilling fluid from each selected sample bottle such that, for each selected sample bottle, the pressure difference threshold is reached and a sample from the body of fluid is acquired.

13 Claims, 24 Drawing Sheets

Related U.S. Application Data

(60) Provisional application No. 62/465,232, filed on Mar. 1, 2017.

(51) Int. Cl.

| | |
|---|---|
| *C12M 1/24* | (2006.01) |
| *C12M 1/26* | (2006.01) |
| *C12M 1/32* | (2006.01) |
| *C12M 1/38* | (2006.01) |
| *G01N 1/28* | (2006.01) |
| *G01N 21/31* | (2006.01) |
| *G01N 21/64* | (2006.01) |
| *G01N 21/83* | (2006.01) |

(52) U.S. Cl.
CPC .............. *C12M 1/38* (2013.01); *C12M 23/08* (2013.01); *C12M 33/06* (2013.01); *C12M 33/07* (2013.01); *C12M 33/12* (2013.01); *G01N 1/28* (2013.01); *G01N 21/3151* (2013.01); *G01N 21/645* (2013.01); *G01N 21/6486* (2013.01); *G01N 21/83* (2013.01)

(58) Field of Classification Search
CPC ...... C12M 33/06; C12M 33/07; C12M 33/12; G01N 1/28; G01N 21/3151; G01N 21/645; G01N 21/6486; G01N 21/83
See application file for complete search history.

(56) References Cited

U.S. PATENT DOCUMENTS

| | | | |
|---|---|---|---|
| 8,373,861 | B2 | 2/2013 | Kanipayor et al. |
| 8,380,446 | B2 | 2/2013 | Mostowfi et al. |
| 11,618,870 | B2 | 4/2023 | Angelescu et al. |
| 2001/0037693 | A1 | 11/2001 | Smith et al. |
| 2003/0042021 | A1 | 3/2003 | Bolze et al. |
| 2007/0009377 | A1 | 1/2007 | Goodrich et al. |
| 2009/0126996 | A1 | 5/2009 | Villareal et al. |
| 2013/0260417 | A1* | 10/2013 | Nijak, Jr. ........... G01N 21/6456 |
| | | | 435/39 |
| 2014/0212986 | A1 | 7/2014 | Angelescu et al. |
| 2014/0345860 | A1 | 11/2014 | Van Zuilekom et al. |
| 2015/0049335 | A1 | 2/2015 | Maselli et al. |
| 2016/0161404 | A1* | 6/2016 | Marshall ................ G16B 50/30 |
| | | | 702/19 |

OTHER PUBLICATIONS

Baudart et al., "Rapid detection of *Escherichia coli* in waters using fluorescent in situ hybridization, direct viable counting and solid phase cytometry," J. Appl. Microbio., vol. 109, No. 4, pp. 1253-1264 (2010), 13 pages.

Baudart et al., "Rapid enumeration of *Escherichia coli* in marine bathing waters: potential interference of nontarget bacteria," J. Appl. Microbio., vol. 107(6), pp. 2054-2062 (2009), 9 pages.

Bergeron et al., "Rapid monitoring of *Escherichia coli* and *Enterococcus* spp. in bathing water using Reverse-Transcription-quantitative PCR," Int. J. Environ. Health, vol. 214(6), pp. 478-484 (2011), 7 pages.

Briciu-Burghina et al., "Continuous fluorometric method for measuring B-Glucuronidase activity: comparative analysis of three fluorogenic substrates," Analyst, vol. 140(17), pp. 5953-5964 (2015), 18 pages.

Heery et al., "ColiSense, today's sample today: A rapid on-site detection of $\beta$-$_D$-Glucuronidase activity in surface water as a surrogate for *E. coli*," Talanta, vol. 148, pp. 75-83, (2016), 11 pages.

Lopez-Roldan et al. "On-line bacteriological detection in water," TrAC Trends in Analytical Chemistry, vol. 44, pp. 46-57 (2013), 12 pages.

Noble et al., "A review of technologies for rapid detection of bacteria in recreational waters," J. Water Health, vol. 03.4, pp. 381-392 (2005), 12 pages.

Wildeboer et al., "Rapid detection of *Escherichia coli* in water using a hand-held fluorescence detector," Water Research, vol. 44, No. 8, pp. 2621-2628 (2010), 8 pages.

US EPA Report: "Guidelines Establishing Test Procedures for the Analysis of Pollutants; Analytical Methods for Biological Pollutants in Ambient Water; Final Rule", U.S. Federal Register 40 CFR Part 136 vol. 68, No. 139 (2003), 12 pages.

* cited by examiner

Sample temperature

1801

1805

FIELD-DEPLOYABLE MULTIPLEXED SAMPLING AND MONITORING DEVICE AND BACTERIAL CONTAMINATION MEASUREMENT METHOD

CROSS-REFERENCE TO RELATED APPLICATIONS

This application is a divisional of U.S. patent application Ser. No. 15/909,523, filed Mar. 1, 2018, entitled "Field-deployable Multiplexed Sampling and Monitoring Device and Bacterial Contamination Measurement Method," which in turn claims priority from U.S. provisional patent application Ser. No. 62/465,232, filed Mar. 1, 2017, entitled "Field-deployable Multiplexed Sampling and Monitoring Device and Bacterial Contamination Measurement Method," each of which is hereby incorporated herein by reference in its entirety.

TECHNICAL FIELD

The present invention relates to a field-deployable multiplexed sampling and monitoring device, which may be used to sample and monitor a body of fluid autonomously, with no cross-contamination and at different depths. Additionally, a sample preparation and analysis module and methodology is provided that allows a sample to be mixed with a reagent and incubated for a period of time, while in parallel performing wavelength-specific optical measurements on the sample.

BACKGROUND ART

In many fields, manual sampling followed by different types of laboratory analyses is required to perform monitoring of water quality parameters. Such is the case for many applications including drinking water, wastewater, environmental, recreational, coastal water and industrial process water monitoring. Such sampling and analysis operations are both equipment and labor intensive, requiring significant resources and trained personnel, which is costly and time consuming. In addition results may not be fully representative of the environment where the samples were collected due to improper sampling chain-of-custody; which can lead to contamination of the sample during sampling acquisition, or to temperature changes and sample degradation processes during transportation to the laboratory. Chemical equilibrium may be affected, living matter in the sample (e.g. bacteria, algae) may evolve (multiply, or die) and consume nutrients from the sample, and interactions of the sample with tubing and container materials may lead to adsorption of certain species onto, or release from, the container or tubing walls. In order to avoid such sample degradation, additional measures need to be taken, such as sample refrigeration, or the addition of different types of chemicals such as fixing agents. This requirement further increases the complexity and logistics of sample collection and transport.

Often, the events that require monitoring may occur at unpredictable times (such is the case with accidental pollutions and storms), or may require a time-series of samples to provide information regarding composition at different times throughout the duration of an event (allowing recording of pollutographs). This may require personnel to be dispatched rapidly and for extended lengths of time, with high associated costs and difficult logistical requirements. Alternatively, it is possible to use automatic sampling equipment (auto-samplers) that can be triggered remotely by external command, by a sensor (such as a precipitation sensor or a turbidity probe) or that can operate on a pre-programmed schedule. Depending on the application, it may be necessary to acquire grab samples (which are representative of the sampled medium at one location and one moment in time), composite samples (multiple samples acquired at regular intervals over a period of time), or flow-proportional composite samples (the sample being collected semi-continuously over a period of time, at an average intake rate that is proportional to the water flow rate measured at the sampling point). Adaptive sampling is required in certain applications (the start of the sampling operation being triggered by a sensor reading).

Such auto-samplers should be as versatile as possible. In particular, they should be easy to install and retrieve. They should be capable to sample in all meteorological conditions, at surface or various depths, near or far away from shore, and without needing external power. The samples should be representative of the medium where the sampler is deployed. The sampling mechanism should not introduce cross-contamination between consecutive samples, especially if monitoring pollutants at trace levels is important.

Sampling in open waters may require access to suitably equipped boats, which can introduce important additional costs. The complexity of sampling and analysis operations can create a logistical nightmare, with strong potential for human errors. Personnel risks inherent to such operations are also significant, especially if sampling is performed at night, in open waters from floating platforms such as boats or barges, or during storm events. Certain types of pollution may pose specific risks as well, such as explosion, fire, chemical, radioactive or biological dangers.

Specific types of pollution, such as offshore oil leaks, may require monitoring a large area, in open water conditions, prior to, during, and after certain events or after pollution treatments are applied. For example, multiple synchronized samples at different locations and depths around an off-shore oil platform may be required prior to the start of exploration and drilling operations (in order to establish a baseline), during the drilling phase (when risks of leaks are high, involving both crude oils and different drilling fluids or chemicals used for treatment), during the completion phase, during de-commissioning operations at the end of the well's life, as well as for long-term monitoring throughout the operational production phase of the well.

Similarly, whenever accidental pollution occurs in open waters, such as an oil spill from a tanker or platform, there is a need to quickly deploy monitoring equipment at different locations around the perimeter of the spill in order to assess the extent and progression of the damage over time, and evaluate the efficiency of remedial operations being undertaken (such as dispersant treatments from boats or aircraft). Typically such monitoring needs to be able to assess the presence of hydrocarbons in the top of the water column, and be able to collect samples at different locations and depths prior, throughout, and after the treatment operation is performed. Such systems should ideally monitor one or several pollution indicators, such as presence of fluorescence, changes in pH, or other suitable parameters. Whenever certain conditions are met, the system should be able to automatically collect one or multiple samples. Whenever such pollution events occur, rapid intervention is of the essence, with the need for monitoring systems that are capable of simple and rapid deployment and retrieval, and ideally of wireless communication even when land-based networks are unreachable.

Other types of pollution, such as natural seeps, may require long-term monitoring, and sampling whenever certain conditions are met (for example, whenever the fluorescence level recorded by a fluorimeter reaches a threshold indicating presence of crude oil).

Currently-used autosamplers are not submersible, and they generally use a hose extending from the unit to the water body and either vacuum or peristaltic pumps in order to pull the sample from the water body to the sampler. Such samplers are relatively difficult to install and limitations exist on the maximum installation height, due to limited pump performance combined with cavitation that may occur in the tubes. All samples circulate through the same sampling tube, which can lead to severe cross-contamination. Cleaning procedures therefore need to be programmed in the device. Such simple cleaning (i.e. blowing air or pumping in reverse) may not be effective in removing certain types of contamination, in particular: oil films that may stick to tubing material, bacteria which may create colonies in the tubes, chemicals and trace compounds which may adsorb or otherwise attach to the walls of the tubing or of the pump. In addition, particles in suspension may not travel at the same speed as the water in the tubes, which may lead to non-representative sampling. Such a sampler cannot sample at different depths, so multiple units need to be used for that purpose. Finally, if power and communication lines are not available, such a sampler will require an additional battery and wireless transmitter, which are typically not integrated in the sampler unit but are separate units of a certain size and weight, which further complicates the installation process. Installation requires time and resources, and cannot be rapidly performed in crisis situations. The use of such instruments in open seas requires an equipped boat, or availability of other type of sea-capable floating platform, at significant expense. These limitations can be taxing for many of the applications previously described.

Some applications (such as: drinking water quality assurance, aquaculture, wastewater monitoring, environmental monitoring, recreational water monitoring, etc) require microbiological analysis of the water to measure the presence and concentration of pathogens such as Enterococci, fecal coliforms, *E. Coli* and other bacteria or viruses. Such pathogens can introduce significant health risks to end users of the water, and measurements are often required for compliance with local, regional or federal law. These measurements can also prove useful for operational purposes, e.g. to improve the water treatment processes, or minimize risks of further contamination.

Such microbial analysis typically require transport of the sample from the collection site to a laboratory, within a few hours of collection and in refrigerated conditions to allow minimal evolution of bacteria within the sample over time. Measuring the bacteria present in water then requires laboratory analysis to be performed. Several techniques are in use today for measuring bacteria such as *E. Coli* or coliforms in general, of which the most widely used are summarized below along with the typical duration of the procedure:

Membrane filtration (optional), and plating on AGAR medium in a Petri dish followed by incubation and colony counting (requires 24-48 h)

Measurement of enzymatic activity by bacterial culture in growth media containing specific enzyme substrates that are linked to certain chromogens and/or fluorogens produced by the bacterial metabolism, followed by incubation and visual confirmation of absorbance and/or fluorescence (requires 18-24 hours, and is used as a presence/absence test. Sample may be divided in multiple compartments or wells to provide some quantitative analysis)

DNA-based analysis involving PCR in different forms (quantitative PCR or digital PCR) (requires 12 hours)

Rapid methods based on direct enzymatic activity measurements using fluorogens, with or without cell lysis, and no culture (2-4 hours, but does not have the same specificity to *E. Coli* as a PCR- or culture-based method. Not an approved method.)

Many of these techniques cannot currently be employed directly in the field, and for approved methods, results are only available after many hours. Combining sample collection, transport, preparation and measurement time, a realistic estimate of the duration from sample to report is of 24 to 36 hours. Sometimes, additional confirmation tests need to be performed, which may further increase this duration.

Such long durations are not well suited for active management of sites. In addition, the costs of regular monitoring can be high: a single routine laboratory analysis may cost upward of $50, and if a report is needed urgently, costs may increase by an order of magnitude. There is therefore a need for rapid detection methods integrated in automated measurement equipment, which can achieve the same specificity as the laboratory methods but produce results in a few hours only, at lower cost per analysis, and without the need for specially equipped laboratories with trained personnel. Such devices may be used either as accurate measurement devices, or as alert stations to give early warning of microbiological contaminations.

Several rapid on-line *E. coli* quantification techniques have been reported (see, for example, R. Lopez-Roldan, P. Tusell, S. Courtois and J. L. Cortina, "On-line bacteriological detection in water," Trends Anal. Chem., vol. 44, pp 46-57, 2013, which is hereby incorporated herein by reference in its entirety), and some have been applied to environmental or recreational water quality monitoring (see, for example, R. T. Noble and S. B. Weisberg, "*A review of technologies for rapid detection of bacteria in recreational waters,*" J. Water Health, pp 381-392, 2005, which is hereby incorporated herein by reference in its entirety). Such techniques use a variety of analytical methods ranging from simple light scattering or direct color and/or fluorescence measurements (see, for example, Andy Baker, Susan A. Cumberland, Chris Bradley, Chris Buckley, John Bridgeman: "*To what extent can portable fluorescence spectroscopy be used in the real-time assessment of microbial water quality?*" Science of the Total Environment 532, pp. 14-19 (2015), which is hereby incorporated herein by reference in its entirety), to complex molecular techniques. Some rapid methods, such as Reverse-Transcription Quantitative PCR (see, for example, P. Bergeron, H. Oujati, V. Catalalan Cuenca, J. M. Huguet Mestre, S. Courtois, "*Rapid monitoring of Escherichia coli* and *Enterococcus* spp. *in bathing water using Reverse-Transcription-quantitative PCR*", Int. J. Environ. Health, vol. 214, pp 478-484, 2011, which is hereby incorporarated herein by reference in its entirety) and direct measurement of enzymatic activity [see, for example: J. Baudart, P. Servais, H. de Paoli, A. Henry and P. Lebaron, "*Rapid enumeration of Escherichia coli in marine bathing waters: potential interference of nontarget bacteria,*" J. Appl. Microbio., vol. 107, pp 2054-2062, 2009; D. Wildeboer, L. Amirat, R. G. Price, and R. A. Abuknesha, "*Rapid detection of Escherichia coli in water using a hand-held fluorescence detector,*" Water Research, vol. 44, no. 8, pp. 2621-2628 (2010); C. Briciu-Burghina, B. Heery, F. Regan: "*Continuous fluorometric method for measuring β-glu-*

5
6 curonidase activity: comparative analysis of three fluoro-genic substrates", Analyst 140 (17) pp. 5953-5964 (2015); and B. Heery, C. Briciu-Burghina, D. Zhang, G. Duffy, D. Brabazon, N. O'Connor, and F. Regan, "ColiSense, today's sample today: A rapid on-site detection of β-d-Glucuroni-dase activity in surface water as a surrogate for E. coli," Talanta, vol. 148, pp. 75-83, (2016), each of which is hereby incorporated herein by reference in their entirety) can pro-vide initial results in as little as 4 hours, but relatively complex sample pre-treatment is required and the techniques are not easy to adapt for fully-autonomous unattended operation. More importantly, such techniques may overes-timate the bacterial load by counting viable as well as dead cells, and may be subject to interference from other bacteria (particularly for enzymatic measurements involving no growth step). More specific molecular biology methods based on Fluorescent In-Situ Hybridization have been devel-oped as well (see, for example, J. Baudart and P. Lebaron, "Rapid detection of Escherichia coli in waters using fluo-rescent in situ hybridization, direct viable counting and solid phase cytometry," J. Appl. Microbio., vol. 109, no. 4, pp. 1253-1264, 2010, which is hereby incorporated herein by reference in its entirety) but their significant complexity limits them to academic laboratory usage for the moment. Defined Substrate Technology (DST), involving a selective growth medium specific to the bacteria of interest and containing specific enzyme substrates that are linked to certain chromogens and/or fluorogens that are produced by the bacterial metabolism, stands out as a reliable detection technique; multiple quantification methods using DST assays and the MPN technique exist (some miniaturized using microplates) (see, for example: US EPA Report: "Guidelines Establishing Test Procedures for the Analysis of Pollutants; Analytical Methods for Biological Pollutants in Ambient Water; Final Rule", U.S. Federal Register 40 CFR Part 136 Vol. 68, No. 139 (2003); and "Water quality—Enumeration of Escherichia coli and coliform bacteria—Part 2: Most probable number method", NF EN ISO 9308-2, "Water quality—Detection and enumeration of Escherichia coli and coliform bacteria—Part 3: Miniaturized method (Most Probable Number) for the detection and enumeration of E. coli in surface and waste water" NF EN ISO 9308-3, each of which is hereby incorporated herein by reference in its entirety). Some commercial sensors automate the defined substrate technology method, and provide bacterial quanti-fication based on the time of absorbance and/or fluorescence appearance, but are not suited for field deployment (see, for example, http://adasaproducts.com/en/portfolio/aquabio/, which is hereby incorporated herein by reference in its entirety).

A number of devices for automated bacterial measure-ments exist, as shown above. These are generally based on automating some of the general techniques mentioned ear-lier. A number of difficulties remain however, which are related to field deployment of such devices. For example, often such devices are not fully automated (requiring human intervention at different stages), or cannot be operated on battery (requiring some sort of facility directly at the point of measurement). They are not submersible, and they often do not integrate sample acquisition and preparation capa-bilities (e.g. automatic mixing with a specific reagent), especially when monitoring the natural environment. Effects of sample properties, such as suspended solids and particles, or water temperature, may adversely affect the measurement or its ultimate accuracy. The difficulty of decontamination and cleaning may further complicate field operation for such an instrument. Such devices often lack the capability to send data or alerts in real time, which limits their utility as microbiological alert stations.

It is often important to be able to monitor events bacterial pollution on a time scale that is shorter that the typical measurement time required by current automated bacterial measurements. Such is the case with rapid discharges during combined sewer overflow events, or during storms, which may quickly contribute significant bacterial pollution to the waterways. Current devices do not allow for such dynamical monitoring.

Bacterial monitoring needs often to be performed in remote field locations, without power or wired communica-tion infrastructure. Examples could include monitoring bac-terial water quality at a farm site (irrigation water monitor-ing), at an aquaculture site, at a remote bathing site, on a water body, on a buoy.

As far as the current quantitative bacterial measurement methods are concerned, many rely on the most probable number (MPN) method, where a number of wells are filled with sample, each acting as a separate "incubator" or "reac-tor" which can give a presence or absence response. Based on the number of wells that record presence of bacteria, it is possible to infer statistically the most probable number of bacteria initially present in a given volume of sample. This method is limited as far as the concentration range is concerned: a sample that is too concentrated will record presence in nearly every well, which limits the quantifica-tion capability. Therefore, to cover the full range of possible concentrations (typically covering several orders of magni-tude), it may be required to perform multiple dilutions of the sample, and measure each dilution independently. The same is true of plating methods—if a sample that is too concen-trated is measured, the full plate will be covered in colonies, making counting and quantification impossible. Similar issued exist when a sample is too diluted, which may require concentrating the bacteria by filtering larger volumes of sample. An additional issue exists with such quantification systems: bacterial colonies aggregated into a particle are counted as a single bacterium. Therefore, if the water to be analyzed contains microbial charges in particulate form, such methods tend to systematically underestimate the microbial concentration. A third issue is related to the fact that accurate results are only available after an incubation time equal to the maximum measurement time.

PCR-based methods can be highly specific to the strain or type of bacterium of interest. However, the complex sample preparation and treatment requirements make this method often impractical for most field implementation. Another disadvantage is that such techniques may also detect DNA matter from dead cells, and therefore cannot differentiate between active and inactive cells. Rapid measurements based on enzymatic activity measure the total activity of certain enzymes that are preponderantly present in the target bacteria, but which cannot be differentiated from similar enzymes present in other types of microorganisms, or even inside dead, inactive cells. Such measurements therefore do not have the specificity requirement for the target bacteria (e.g. E. Coli), which may result in false positives—the measurement acts therefore only as a proxy for target bacteria (E. Coli) presence, and depends on the local water microbiological matrix. Such tests typically require confir-mation by other complementary measurements with improved specificity. Rapid enzymatic activity measure-ments may therefore be acceptable for an alert station, but do not provide an accurate sensor for quantification of the living target bacteria concentration. The measurement requires a very sensitive and accurate determination of enzymatic activity over time, which is often measured by fluorescence of an enzymatic activity byproduct. A highly sensitive fluorescence detector is required, and the measurements may be affected by sample properties, such as turbidity or color, requiring corrections; the measurement also requires sample pre-treatment, which may be difficult to perform in a fully automated fashion.

Any automated microbiological measurement station is prone to contamination coming from previous samples. For example, bacterial colonies can form on components within the instrument that come in contact with a previous sample. Another issue that all such instruments face, especially for deployment in the natural environment, is generation of waste, which should be completely eliminated, neutralized, or contained.

SUMMARY OF THE INVENTION

Various embodiment of the invention provide sampling devices capable of performing sample acquisition operations in an automatic fashion, directly in-situ, while avoiding the avoiding the above described issues. The sampling devices may be configured to include any or all of the following features:
  submersible and/or floatable
  fully self-contained and capable of operate on battery with long power autonomy
  robust, and not affected by adverse weather or sea conditions
  capable of being remotely controlled and to quickly respond to a sampling request. Such remote control could be wired, or wireless using e.g. radio, optical, cellular, satellite or acoustic communication
  capability to be pre-programmed and acquire samples on a schedule
  configured to use different fluid conduits and different containers for each independent sample, so as not to introduce cross-contamination between samples
  should not allow fluid contact with the sampling conduits and container prior to the sampling operation
  configured to grab, composite and/or adaptive sampling, depending on application configured to perform certain filtration or pre-concentration operations on each sample
  configured to collect samples from different depths, including near surface and, typically, in the upper 10 meters of the water column
  configured to record GPS coordinates as well as a time-stamp for each collected sample
  capable to communicate to an operator (either wirelessly or whenever a cable connection is established) the status of the system and of its operational parameters (i.e. battery voltage, temperature, signal strength, etc.); the measurements obtained from whatever sensors may be attached to the system; information about on-going sampling operations; list of available containers for sampling; chain of custody data for each sample such as container number, location, depth, timestamp, etc.
  easy to install or deploy, and easy to retrieve with minimum use of external equipment, and should be able to broadcast information about GPS position for easy recovery; systems may also have beacon lights or radio beacons for easy identification and retrieval
  configured to maintain samples, after acquisition, either at the temperature of the water or in refrigerated conditions, so as to minimize sample degradation capable of preserving samples, after acquisition, by automatic addition of a fixing agent, biocide or other chemical depending on the application, to avoid sample evolution.

Furthermore, various embodiments of the invention provide for an automated microbiological measurement method, instrument and system that allows for rapid quantification and differentiation of bacteria, directly in-situ, with minimal maintenance requirements. To respond to the various requirements of different applications, and eliminate the disadvantages of existing methods and instruments, the instrument may be configured to satisfy any or all of the following:
  configured to operate directly in the body of water to be analyzed (to act as an alert station in the natural environment for swimming areas, source water monitoring, aquaculture, agriculture, irrigation water monitoring, storm water monitoring, wastewater outflow monitoring, etc), or integrated to a measurement station, in an industrial setting, within a treatment facility, or in the drinking water distribution network
  integration of sampling capabilities, as well as all the sample preparation and treatment operations required (e.g. mixing with reagents, sample assurance, volume control, incubation with accurate temperature control, filtration, etc.)
  configured to eliminate, or minimize, any possibility of cross-contamination between different samples, such as for example, residue from one highly-charged sample contaminating subsequent samples and leading to incorrect measurements.
  waste should be well controlled, and contained within the device, or eliminated safely
  easy to maintain and decontaminate for redeployment directly in the field by a non-specialized technician, and ideally be amenable to operation using only one-time-use (consumable) cartridges
  be based on a method that satisfies the following criteria:
    capable to provide quantification of all viable target bacteria in the medium, including those aggregated on particles, with no, or only minimal interference from other species of microorganisms or from dead bacteria
    capable to provide quantification of dispersed bacteria only (eliminate the aggregated portion)
  configured to be able to communicate data remotely, bi-directionally, to the cell phone of a user or operator, or to a server
  configured for rapid measurement—results in cases of severe contamination should be available and transmitted wirelessly as soon as possible to enable immediate response and remedial action
  configured to enable quantification over a large range of bacterial concentrations (5-6 orders of magnitude), without requiring successive sample dilutions
  does not require complex sample preparations steps
  configured to be highly robust and not require ultrasensitive optical determinations, which could be affected by various un-related optical sample properties and could be difficult to reliably implement in a fully autonomous field sensor
  configured to perform multiple measurements in parallel, and thus monitor rapid bacterial dynamics, which may happen during combined sewer overflows, accidental discharges, or storms configured to operate in real field environments, and be able to withstand variations in temperature and humidity, precipitations, shocks, water immersion.

More particularly, in accordance with an embodiment of the invention, a system for processing samples from a body of fluid is provided. The system includes one or more sample bottles for acquiring a sample from the body of fluid. Each sample bottle initially retains a pre-filling fluid. Each sample bottle includes a fluidic inlet port and a bottle outlet port. Each sample bottle has an inlet check valve coupled to the fluidic inlet port, the inlet check valve configured to allow fluid from the body of fluid into a sample bottle via the fluidic inlet port when the pressure difference between the body of fluid and fluid within the sample bottle reaches a threshold. The system further includes at least one pump, the bottle outlet port of each sample bottle selectively coupled to the at least one pump via a different control valve. The at least one pump is configured, in a first configuration, to remove prefilling fluid from each selected sample bottle such that, for each selected sample bottle, the pressure difference threshold is reached and a sample from the body of fluid is acquired.

In accordance with related embodiments of the invention, the at least one pump may include a vacuum pump and a pressure pump, and the pressure pump acts to pressurize the selected sample bottle(s). The at least one pump may be a bidirectional pump.

In accordance with further related embodiments of the invention, the at least one sample bottle may have an associated pumping filter that allows the pre-filling fluid to pass but not the fluid from the body of fluid, the pumping filter positioned such that any fluid that has entered the at least one sample bottle from the body of fluid does not pass through the control valve associated with the at least one sample bottle. The pumping filter may be positioned or extended within the sampling bottle such that only a predetermined volume of fluid from the body of fluid is allowed to enter the sampling bottle. The pre-filling fluid may be a gas, and after the predetermined volume of fluid from the body of fluid has entered the sampling bottle, a volume of pre-filling gas remains in the sampling bottle.

In accordance with still further related embodiments of the invention, the system further includes at least one controller for controlling the at least one pump and the control valves. Each sample bottle may include a sampling tube that extends the fluidic inlet port distally from the sampling bottle, the sampling tube length allowed to vary between different bottles. The system may include a disposable component that is installed prior to deploying the system to obtain a sample and discarded after the sample has been obtained, the disposable component including at least two of the following items: the sampling bottle, the inlet check valve, a pumping filter, an inlet filter, tubing, a flush valve, reagent, a moving partition, a piston, a bag, a diaphragm, a sealing mechanism, and a locking mechanism for securing the disposable component to the system, or combinations thereof.

In accordance with yet further embodiments of the invention, at least one of the sample bottles may include a flush port that is fitted with a flush check valve, the flush check valve configured to allow sample fluid to exit the bottle. At least one of the sample bottles may include a movable partition, piston, bag and/or diaphragm that separates the bottle outlet port from the fluid inlet port. The sample bottle may include a fixing agent, a chemical reagent, a bio-reagent, a growth medium, a biocide, a preservation substance, or combinations thereof, placed within the sample bottle prior to acquiring a sample so as to mix or react with the sample fluid once a sample is acquired. The system may further include a conduit, pipe or manifold through which the body of fluid can flow, the fluidic inlet port of each sample bottle connected to said conduit, pipe or manifold.

In accordance with further related embodiments of the invention, the system may further include a temperature control apparatus for controlling the temperature of sample fluid in at least one of the one or more sampling bottles. The temperature control apparatus may include a controller, the controller configured to: determine a total amount of heat needed to raise the temperature of sample fluid in a sampling bottle to a desired temperature; and initially inject the determined total amount of heat into the sample fluid as quickly as the temperature control apparatus is operationally capable.

In accordance with yet further related embodiments of the invention, the system further includes at least one optical sensor for measuring optical properties of sample fluid in a sampling bottle, wherein the optical sensor includes at least one of: a light source, an optical setup, a light detector, or combinations thereof. The light source may be an incandescent source, a halogen lamp, a gas discharge lamp, a light emitting diode, a laser diode, or combinations thereof. The optical setup may be an arrangement of optical alignment hardware, optical waveguides, optical fibers, liquid waveguides, light channels, optical filters, neutral density filters, interference filters, quarter wave plates, polarizers, low-pass optical filters, band-pass optical filters, high-pass optical filters, mirrors, monochromators, collimators, diffraction gratings, apertures, lenses, active optical components, passive optical components, or combinations thereof. The light detector may be a photodiode, a phototransistor, a cascade-effect photodiode, a photomultiplier, a photoamplifier, a CMOS sensor, a CCD sensor, a spectrometer, a pyroelectric detector, a bolometer, or arrays or combinations thereof. The system may further include a controller configured to determine when sample fluid in a sampling bottle has been obtained based on output from the at least one optical sensor. The controller may be configured to determine bacterial concentration of sample fluid in a sample bottle as a function of fluorescence and/or absorbance signal appearance times obtained from the at least one optical sensor during incubation of the sample fluid. The optical sensor may be configured to determine at least one optical property such as sample absorbance at certain wavelengths, sample fluorescence upon excitation at certain wavelengths, sample turbidity, sample index of refraction, and combinations thereof.

In accordance with related embodiments of the invention, the optical sensor for measuring absorbance may be configured to use multiple wavelengths of light, which may be selectively sensitive certain optical properties of the sample. As an example, a first wavelength L1 may be chosen to be sensitive to a certain sample coloring agent which absorbs light at that wavelength (the sensor measuring a significant absorbance increase at L1 in the presence of the coloring agent), but does not absorb light at a second wavelength L2 (the sensor not registering any absorbance change in the presence of the reagent). Light at both wavelengths L1 and L2 may be scattered by particles present in the sample, and thus respond identically to turbidity and measure identical absorbance increases at L1 and L2 in presence of turbidity. By subtracting the absorbance measured at L2 from the absorbance measured at L1 for a given sample, the contributions corresponding to turbidity will subtract out and cancel, whereas the contribution corresponding to the presence of the coloring agent will persist. Thus, by using two appropriately chosen wavelengths, the optical sensor can be made specific to the presence of the coloring agent, but insensitive to turbidity.

In accordance with still further related embodiments of the invention, the system may include a housing, the at least one pump positioned within the housing, and at least one flotation element such that the housing floats in the body of fluid. The system may include a controller configured to activate the pump for a limited duration so as to acquire a known amount of sample.

In accordance with another embodiment of the invention, a method of processing fluidic samples from a body of fluid is provided. The method using at least one pump and one or more sample bottles, each sample bottle initially containing a pre-filling fluid and including a fluidic inlet port and a bottle outlet port. The bottle outlet port of each sample bottle is selectively coupled to the at least one pump via a different control valve. Each sample bottle has an inlet check valve coupled to the fluidic inlet port, the inlet check valve configured to allow fluid from the body of fluid into a sample bottle via the fluidic inlet port when the pressure difference between the body of fluid and within the sample bottle reaches a threshold. The method includes positioning the fluidic inlet port of each sample bottle in the body of fluid. The control valve of at least one of the one or more sample bottles is controlled to couple the bottle output port of the at least one sample bottle to the at least one pump. The at least one pump is configured, in a first configuration, to remove prefilling fluid from each selected sample bottle such that a sample from the body of fluid is acquired in the selected bottle.

In accordance with related embodiments of the invention, the at least one pump includes a vacuum pump and a pressure pump, and the pressure pump acts to pressurize the selected sample bottle(s). The at least one pump may be a bidirectional pump. At least one sample bottles may have an associated pumping filter that allows the pre-filling fluid to pass but not the fluid from the body of fluid, the pumping filter positioned such that any fluid that has entered the at least one sample bottle from the body of fluid does not pass through the control valve associated with the at least one sample bottle. The pumping filter may be positioned or extended within the at least one sampling bottle such that only a predetermined volume of fluid from the body of fluid is allowed to enter the sampling bottle. The pre-filling fluid may be a gas, and after the predetermined volume of fluid from the body of fluid has entered the sampling bottle, a volume of pre-filling gas remains in the sampling bottle. The fluidic inlet port of each sample bottle may be extended via a tube distally from the sampling bottle. The method may include controlling, by a controller, the at least one pump and the control valves.

In accordance with a further related embodiment of the invention, prior to acquiring the sample fluid, at least two of the following: the sampling bottle, the inlet check valve, a pumping filter, an inlet filter, tubing, a flush valve, reagent, a moving partition, a piston, a bag, a diaphragm, a sealing mechanism, and a securing mechanism may be provided as a disposable component. After acquiring the sample fluid, the disposable component is discarded.

In accordance with still further related embodiments of the invention, the method may further include separating the bottle outlet port from the fluid inlet port of at least one of the sample bottles using a moving partition, bag, piston and/or flexible diaphragm. At least one of the sample bottles may include a flush port that is fitted with a flush valve, the method further including pressurizing the at least one of the sample bottles such that fluid exits the sample bottle via the flush port. The method may include providing within the sample bottle a fixing agent, a chemical reagent, a bio-reagent, a growth medium, a biocide, a preservation substance, or combinations thereof and placing it within the sample bottle prior to acquiring a sample so as to mix or react with the sample fluid once a sample is acquired.

In accordance with yet further related embodiments of the invention, the body of fluid may flow through a conduit, pipe or manifold, the method further including connecting the fluidic inlet port of each sample bottle to the said conduit, pipe or manifold, so as to retrieve fluidic samples from the body of fluid in the conduit.

In accordance with further related embodiment of the invention, the method may include controlling the temperature of sample fluid in at least one of the one or more sampling bottles. A controller may determine a total amount of heat needed to raise the temperature of sample fluid in a sampling bottle to a desired temperature; and inject, by a temperature control apparatus, the determined total amount of heat into the sample fluid as quickly as the temperature control apparatus is operationally capable.

In accordance with still further related embodiments of the invention, the method may include measuring optical properties of sample fluid in a sampling bottle using an optical sensor, wherein the optical sensor includes a light source, an optical setup, a light detector, or combinations thereof. The optical sensor may be configured to determine at least one optical property selected from the group consisting of sample absorbance at certain wavelengths, sample fluorescence upon excitation at certain wavelengths, sample turbidity, sample index of refraction, and combinations thereof. A controller may determine when sample fluid in the sampling bottle has been obtained based on output from the at least one optical sensor.

In accordance with yet further related embodiments of the invention, the method may include determining, by a controller, bacterial concentration of sample fluid in a sample bottle as a function of fluorescence and/or absorbance signal appearance times obtained from the at least one optical sensor during incubation of the fluidic sample.

In accordance with still further related embodiments of the invention, the at least one pump, the one or more sample bottles, a controller for controlling at least the pump, the control valves or combinations thereof, are enclosed within the housing. The sample bottles may be located outside the housing, and wherein when the housing is placed in the body of fluid, the sample bottles are submerged in the body of fluid. The sample bottles may be at least partially enclosed within the housing, and wherein the fluidic inlet port of each sample bottle is extended into the body of fluid via a tube. The method may include fully or partially submerging the housing in the body of fluid. The at least one pump may be coupled to a pump exhaust conduit that provides fluidic communication to outside the body of fluid. The method may include positioning the housing outside the body of fluid, with the sample bottles submersed in the body of fluid such that the inlet port of each sample bottle is at a predetermined depth in the body of fluid. The method may include positioning the at least one pump and the sample bottles within a housing, and furthermore, positioning the housing and sample bottles outside the body of fluid, with the fluidic inlet port of each sample bottle extending, via a tube, into the body of fluid to a predetermined depth. The body of water may be drinking water.

In accordance with another embodiment of the invention, a method of quantifying contamination of a fluidic sample by a type of bacteria of interest is provided. The method includes acquiring a sample fluid in a sample bottle. The sample fluid is mixed a reagent providing an optical signature in presence of the bacteria of interest. A fluorescence optical signal and/or an absorbance optical signal from the sample fluid is measured at multiple times using an optical sensor, wherein a minimum of two wavelengths of light are used to measure the absorbance signal, the two wavelengths being selected such that one is more sensitive than the other to the optical signature of the reagent. The sample fluid is incubated prior to, or during, the measuring. Bacterial concentration of the sample fluid is determined as a function of a shape of a fluorescence versus time curve and/or an absorbance versus time curve obtained from the at least one optical sensor during incubation of the fluidic sample.

In accordance with related embodiments of the invention, determining may include comparing the fluorescence and/or absorbance signal appearance times with a calibration curve, the calibration curve based, at least in part, on comparing signal appearance times of a plurality of sample fluids obtained previously with their actual bacterial concentrations determined using another reference technique. The sample bottle may include a growth medium that enables the growth of the bacteria of interest. The system may include further multiple sample bottles, each bottle used to measure a single fluid sample, the system being able to perform multiple measurements in parallel. The may be portable and/or submersible, and configured to operate on battery and transmit data wirelessly.

In accordance with another embodiment of the invention, a system for quantifying contamination of a fluidic sample by a type of bacteria of interest is provided. The system includes a sample bottle into which a sample fluid is acquired, and a reagent providing an optical signature in presence of the bacteria of interest, that is mixed with the sample fluid. An optical sensor obtains a fluorescence optical signal and/or an absorbance optical signal from the sample fluid at multiple times, said optical sensor using a minimum of two wavelengths for measuring the absorbance optical signal, wherein the two wavelengths are selected such that one is more sensitive than the other to the optical signature of the reagent. A temperature controller apparatus incubates the sample fluid. A controller is configured to determine bacterial concentration of the sample fluid as a function of a shape of a fluorescence versus time curve and/or an absorbance versus time curve obtained from the at least one optical sensor during incubation of the fluidic sample.

In accordance with related embodiments of the invention, determining may include comparing the fluorescence and/or absorbance signal appearance times with a calibration curve, the calibration curve based, at least in part, on comparing signal appearance times of a plurality of sample fluids obtained previously with their actual bacterial concentrations determined using another reference technique. The sample bottle may include a growth medium that enables the growth of the bacteria of interest. The system may include further multiple sample bottles, each bottle used to measure a single fluid sample, the system being able to perform multiple measurements in parallel. The may be portable and/or submersible, and configured to operate on battery and transmit data wirelessly.

In accordance with another embodiment of the invention, a system and method includes one or more sample analysis devices for obtaining sample measurements from a body of fluid. A server is in bidirectional communication with the one or more sample analysis devices. A controller is configured to trigger, based on at least one condition, the one or more sample analysis device to obtain the sample measurements. The controller is further configured to analyze the sample measurements to determine if an alert condition is met, and if so generate a user alert. The controller is located in the server, at least one of the one or more sample analysis devices and/or a device remote from the server that is in communication with the server.

BRIEF DESCRIPTION OF THE DRAWINGS

The foregoing features of embodiments will be more readily understood by reference to the following detailed description, taken with reference to the accompanying drawings, in which:

FIG. 6*b* shows a sampling device with the fluid inlet ports of the different sampling bottles connected to a fluid manifold, allowing each sample to be acquired from the fluid line within said manifold, in accordance with an embodiment of the invention;

DETAILED DESCRIPTION OF SPECIFIC EMBODIMENTS

In illustrative embodiments of the invention, a multiplexed sampling system and methodology enables in-situ collection of multiple uncontaminated fluid samples autonomously, with no cross-contamination, and at different depths within the water column as desired. The multiplexed sampling system described herein can be deployed for sampling directly in a body of water, (such as, without limitation: lakes, rivers, canals, collection tanks, ponds and/or coastal waters) or directly from a conduit through which water is physically transported (distribution network, water treatment facilities, etc.). Furthermore, a sample preparation and analysis module and methodology is presented that advantageously may allow a sample to be mixed with a reagent and incubated for a period of time, while in parallel performing wavelength specific optical measurements on the sample. The optical measurement vs. time data curves may be interpreted to quantify, for example, the concentration of microorganisms of a specific species contained within the acquired sample. Details are described below.

Multiplexed Sampling Device

As used in this description, the term "sampling device" (also called, interchangeably: a sampler; a sampling instrument or system; a sample acquisition instrument, device or system) as used herein shall mean a device capable of acquiring and storing multiple physical fluid samples from a sampling medium (for example, and with no limitations, a body of fluid such as, without limitation, a lake, a reservoir, a tank, a pond, a river, an aquifer, an outflow, coastal water, full-depth ocean water, and/or an open channel) either near surface or at depth; or from a pipe, tubing, closed channel, or any other type of conduit, unless the context otherwise requires.

Additionally, as used in this description, the term "fluid" as used herein shall mean a liquid or a gas, unless the context requires otherwise requires.

Figure 1:
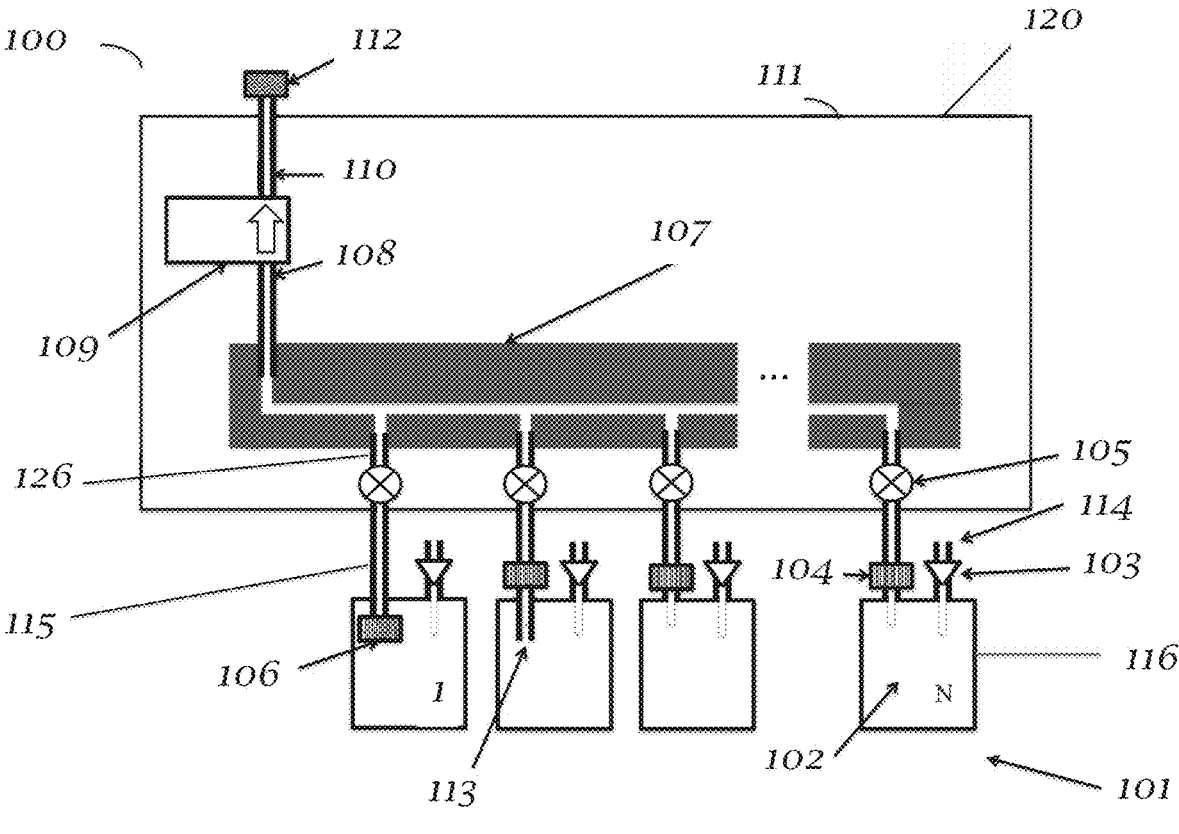
FIG. 1 shows a sampling device deployed near a body of fluid, in this case a liquid sampling medium, to collect samples near the surface of the sampling medium, in accordance with an embodiment of the invention.

FIG. 1 shows a sampling device 100 deployed near a body of fluid 101, in this case a liquid sampling medium, to collect samples near the surface of the sampling medium, in accordance with an embodiment of the invention. The multiplexed sampling device 100 described in the following eliminates many of the disadvantages and shortcomings of existing sampling devices, which were described above.

The multiplexed sampling device 100 includes a pumping module 111 and multiple sampling bottles 102. The pumping module 111 may be surrounded by a housing 120, and may be comprised of a pump 109, a pumping manifold 107 and multiple control valves 105 (valves 1, 2, . . . N), each valve 105 corresponding to a different sampling bottle 102 (Bottle 1, Bottle 2, and so on), thus allowing the capability to multiplex the sampling operations. The pump 109 may have its low-pressure side (or low-pressure pump connection) connected to the pumping manifold 107. Optionally, one or multiple additional protection housings may surround the different components of the sampling device 100 to protect them from shocks and from becoming entangled with floating matter such as sea grass, algae, branches etc., or to provide thermal insulation. The pumping module housing or the protection housing 120 may further include attachment points for physically securing the sampling device 100. The sampling bottles 102 may, optionally, be installed within the pumping module housing 120.

Different types of pumps may be used inside the pumping module 111. In particular, the pumping module 111 may be uni-directional (capable of transporting fluid in a single direction), or bi-directional (capable to transport fluid in both directions). In accordance with an embodiment of the invention, the pump may be, for example, a uni-directional vacuum pump. In this case, the pump's port that is not connected to the pumping manifold 107 (e.g. the high pressure pump connection in the case of the vacuum pump) may be open to the inside of the pumping module housing, or it may optionally be connected, via a tube or conduit, to the outside of the pumping module housing 120 (as shown in FIG. 1). An optional pump exhaust module 112 may be attached to the pump exhaust or to the corresponding tube or conduit, allowing air from the pump to pass, but blocking fluid from entering the pump 109. Such a pump exhaust module 112 may be a hydrophobic porous medium which allows passage of gases but blocks passage of fluids due to capillarity effects, or it may be a one-way check valve allowing passage only in one direction (from the pump moving out in the case of the vacuum pump, and moving in for the pressure pump), or may consist of any other device known to the person skilled in the art and performing a substantially similar function.

Another embodiment of this invention includes the possibility to pressurize the sampling bottles 102 prior to deployment. In this case, a bi-directional pump capable of reverse pumping may be used, to pump air from the pump exhaust module and into different bottles 102 in order to pressurize them prior to deployment.

Figure 2:
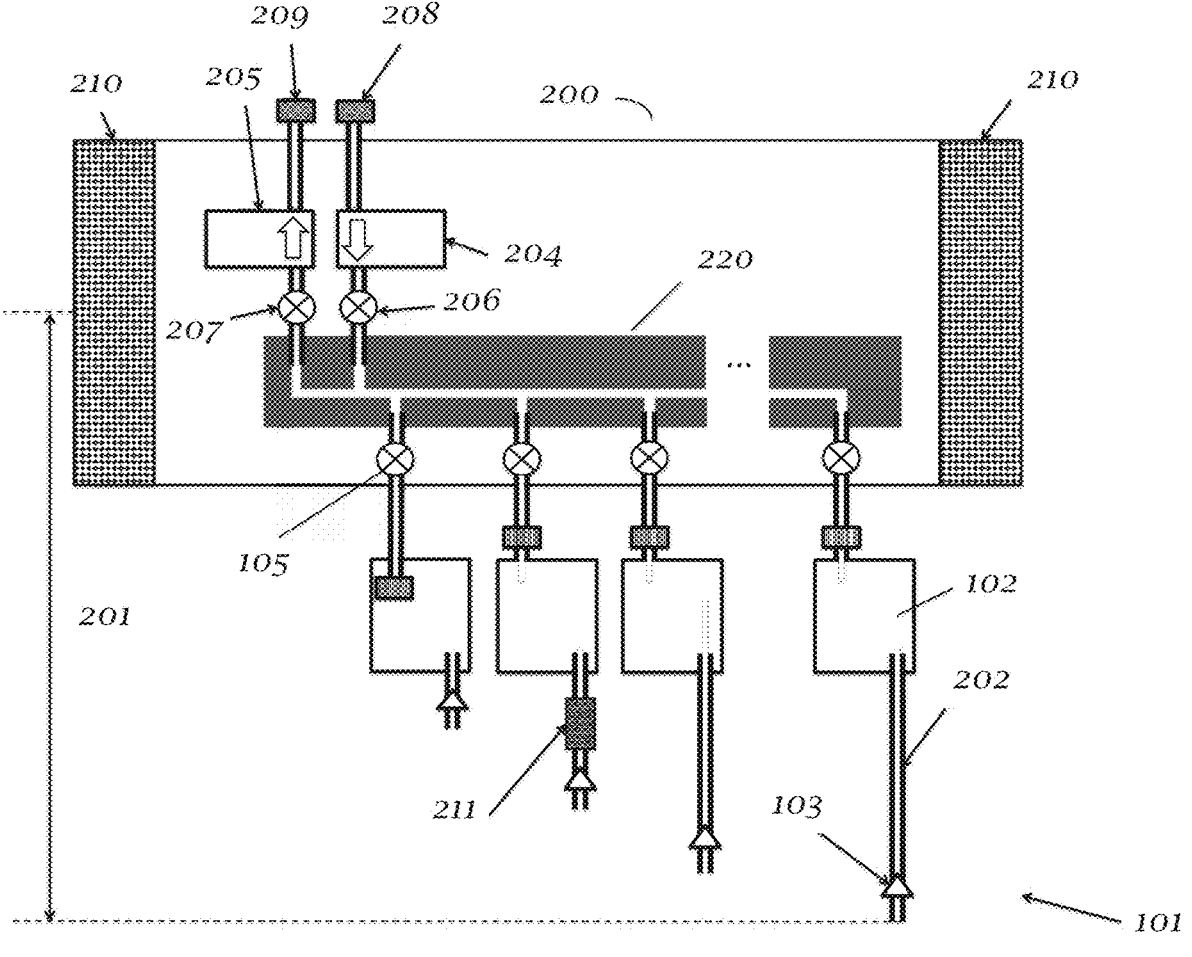
FIG. 2 shows a sampling device that includes two pumps, in accordance with an embodiment of the invention.
Figure 5:
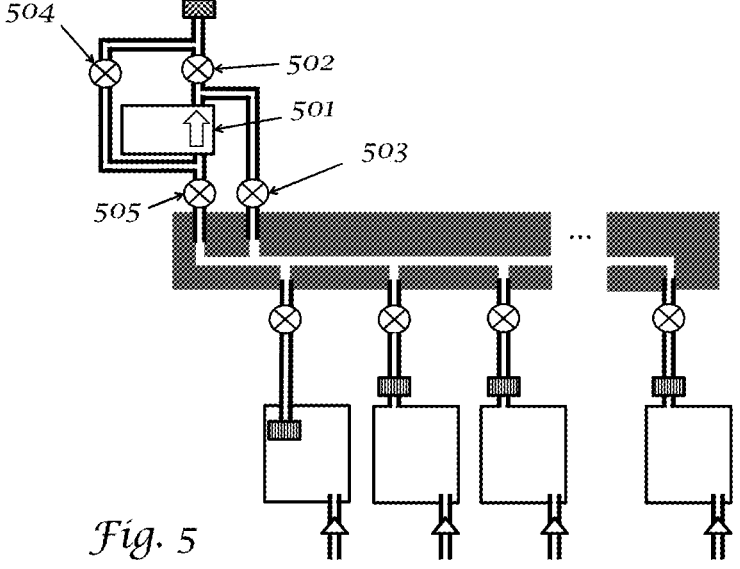
FIG. 5 shows a sampling device that includes a single, bi-directional pump, in accordance with an embodiment of the invention.

FIG. 2 shows a sampling device 200 that includes a second uni-directional pump 204 which acts as a pressure pump, in addition to the uni-directional vacuum pump 205, in accordance with an embodiment of the invention. The pressure pump 204 and the vacuum pump 205 may both be connected, in this case, to the pumping manifold 220 using two valves (master valves) 206 and 207. Alternatively, a single uni-directional pump 501 but capable to provide vacuum at one port (thus working as a vacuum pump) and pressurized air at the opposite port (as a pressure pump) may be used, and a configuration of master valves, as shown in FIG. 5, may be used to select which pump port (pressure or vacuum) is connected to the pumping manifold and which port to the exhaust. In this case, when the pump needs to be operating as a vacuum pump, Master Valves 502 and 505 in FIG. 5 are maintained open, whereas Master Valves 503 and 504 are closed. On the other hand, when the pump needs to operate as a pressure pump, Master Valves 502 and 505 are closed, and Master Valves 503 and 504 and open. It is understood that this configuration of valves is only exemplary, and a person skilled in the art will recognize that many different valve types and valve configurations could be used to achieve similar function. For example, three-way valves may be used in place of simple on-off valves. Similarly, latching valves, or normally open or normally closed valves may be used.

The pumping manifold, the pump, or any other component that can be pressurized by the pressure pump may further be connected to a pressure-relief mechanism, which allows pressurized air to escape if pressure increases past a pre-defined limit. This may provide security against explosion, should the pressure increase in an uncontrolled manner. Such protection may also be provided directly by the pressure pump, in case its maximum achievable pressure is below the dangerous explosion limit.

In accordance with various embodiments of the invention, the fluid to be sampled is a liquid, and a liquid pump may be used inside the pumping module. Such a liquid pump may for example be a peristaltic pump, a centrifugal pump, a turbine pump, or any other type of liquid pump known in the art. Depending on the rotation direction of the peristaltic pump motor, such a pump may pump fluid out of, or into the pumping manifold. The pump port that is not connected to the pumping manifold is, in this case, connected to the outside of the pumping module. A pressure-relief mechanism, as described above, may also be included to provide protection for over-pressurization.

The master valves and control valves described above may be operated using control electronics (not shown graphically) within, for example, a controller, such as to open or close the connection of the vacuum pump or of the pressure pump to the vacuum manifold. Referring back to FIG. 1, the manifold 107 may have multiple ports 126 for the N sampling bottles 102, one port for each bottle 1 . . . N. Between the manifold 107 and each bottle 102 there are N control valves 105, each being able to operate, as instructed by the control electronics, the opening or closing of the connection between the manifold 107 and the respective bottle 102. The master (see FIG. 5, 502-505) and control valves 102 can be any kind of valve known to a person skilled in the art, such as, with no limitation: a solenoid valve, an on-off valve, a three-way valve, a pneumatically or hydraulically-actuated valve, a mechanical valve, a membrane-actuated valve, a capacitive valve, a valve using fluid surface tension effects, a MEMS or microfluidic valve.

The control electronics may be part of the pumping module and is meant to provide communication, sampling control and/or data recording capability. The control electronics, which may be a controller or a control module, may comprise, without limitation, one or several of the following elements: one or multiple electronics boards; real time clock; memory; battery, solar panel, external power connector, or other means of powering the control module; one or multiple processors or microcontrollers, allowing control of the master and control valves, recording of a sampling program, execution of said sampling program at the programmed times, and external communication. The pumping module may further incorporate means of external communication, such as, and without limitation: a serial or parallel communication port; a USB port; a wired or wireless communication modem and corresponding antenna. The pumping module may contain a GSM modem for communicating with a cell phone or with another GSM modem, or may contain other types of radio communication modules such as, with no limitation, Iridium, LoRa or Sigfox, as well as the corresponding antennas. It may also contain a GPS unit and corresponding antenna.

The control electronics may also be connected to one or multiple external sensors, and capable to read the values measured by such sensors. Depending on the measured values, the control electronics may automatically operate the pumping module, so as to trigger, for example, the acquisition of a sample by the sampling device. An algorithm may be implemented inside the control electronics that defines what conditions relating current and past sensors readings result in a sample acquisition operation. Sensors may include, but are not limited to: sensors for measuring fluid level, fluid flow rate, fluid velocity, or for detecting precipitation; sensors for measuring conductivity, pH, salinity, temperature, or other physical parameters of the sampling medium; sensors for measuring chemical composition of the sampling medium; sensors for measuring fluorescence, absorbance, color, turbidity or other optical properties of the sampling medium; sensors for detecting or measuring microbiological contamination; as well as any other types of sensors and measurements devices known in the art.

Multiple sampling devices may be controlled from a single central gateway, which communicates with the devices via a wired or wireless protocol to implement device control and coordinate the sampling operations, and to collect and process optional positioning and fluid sensor data.

The control valves 105 in the pumping module 111 are attached to their respective sampling bottle 102 either directly or using any kind of connecting elements such as tubing, piping, a channel or microchannel, or other type of conduit or combinations thereof known to the person skilled in the art. Such connecting elements may optionally extend into the bottle. The sampling bottle may include a recipient 116 that defines a volume, as well as two bottle connections, a fluidic inlet port 114 and a bottle output port 115. Either bottle connection 114 and 115 may be attached directly to the recipient 116, or to a separate sampling adapter, itself attached to the bottle in an airtight manner. The bottle connections 114 and 115 may be placed at or near the cap of the bottle 102, near the bottom of the bottle 102, or in any other position relative to the bottle 102. The recipient's 116 function is to store the sampled fluid, and it may have any different shape, not necessarily resembling a bottle. It may be made of any material such as and without limitation: glass, metal, plastic, ceramics, composite materials. The recipient may desirably be chemically compatible with the sampling medium, and should not interfere chemically or physically with the compounds of interest in the sample.

The sampling bottles 102 are initially filled with a prefilling fluid which may be a gas (such as air), or a liquid (such as water). Illustratively, in embodiments in which the bottles 102 are pre-filled with a gas, each bottle may be fitted with two connections: a bottle output port 115 that allows the gas to be pumped out of the bottle 102, and a fluidic inlet port 114 that allows the sampled fluid to enter into the bottle 102. The control valves 105 in the pumping module 111 are attached to each bottle's outlet port 115. Optionally, a pumping filter 106 may be installed between the control valve 105 and the bottle 102, positioned, for example and with no limitation, in one of the following positions, without limitation: near the control valve 105; on the connecting element between the valve 105 and the bottle 102; onto the bottle 102 or inside the bottle 102, or onto the sampling adapter (either outside—Bottle N in FIG. 1, or inside the bottle—Bottle 1 of FIG. 1). Said pumping filter 106 is meant to allow gas (e.g., air) to pass through, but stop fluid from the body of fluid/sampling medium 101, thus avoiding flooding the interior of the vacuum pump 109 with fluid. The pumping filter 106 may include, as a non-limiting example, of a hydrophobic porous medium or membrane which allows passage of gases but blocks passage of liquids due to capillarity effects. When the pumping filter 106 is installed inside the bottle 102, the position of the pumping filter 106 may be used to physically stop the pumping of air out of the sampling bottle by the pumping module 111, when the pumping comes in contact with the sampling medium (for example, and without limitation, a liquid such as water), thus being able to dictate an exact sampling volume. An example of such a filter 106 may be a porous membrane made, for example, of PTFE or any other hydrophobic material, and having a pore size that is small enough to block by capillary effects the passage of the fluid to be sampled when undergoing a differential pressure typical of that produced by the vacuum pump 109. The pumping filter 106 may further be extended inside the sampling bottle 113, which allows further control on the sampling volume.

Figure 6:
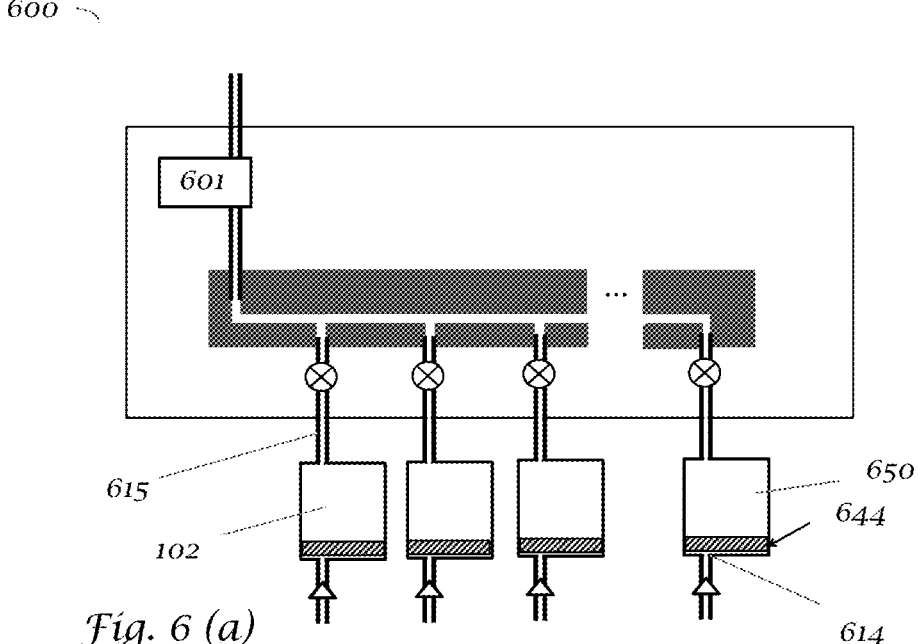
FIG. 6(*a*) shows a sampling device wherein each bottle includes a piston, separating the bottle outlet port from the fluid inlet port, in accordance with an embodiment of the invention.
Figure 6:
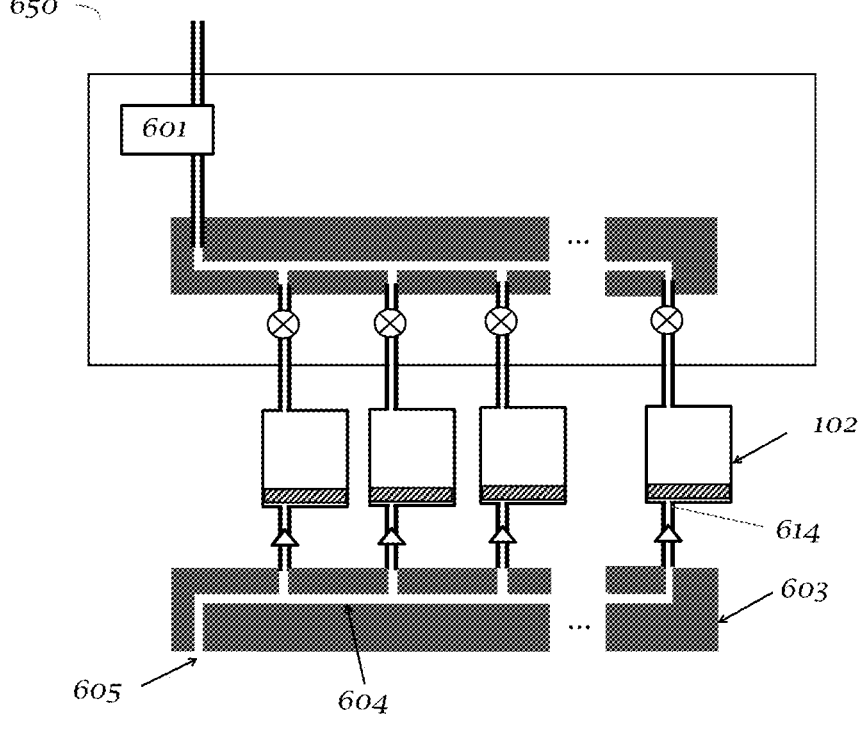

FIG. 6(*a*) shows a sampling device 600 wherein each bottle 102 may include a piston 644, separating the bottle outlet port 615 from the fluid inlet port 614, in accordance with an embodiment of the invention. The piston 644 may be placed initially near the fluid inlet port 614, such that, as sampling fluid enters the cavity, it is completely separated from the pre-filling fluid 650 (which may be either a gas or a liquid). Alternatively, instead of the piston 644, one may use other types of flexible non-permeable elements, such as a bag or a flexible diaphragm, which ensures the same function of separating the sampling fluid from the pre-filling fluid 650 originally present in the bottle 602. Additionally, each bottle 102 may be pre-charged, on the inlet side of the piston 644, with a small amount of fixing agent, biocide, or other such substance or chemical used within the industry to preserve the sample. Said substance or chemical may be placed in the bottle 102 between the piston 644 and the fluidic inlet port 614 prior to deployment. The pump 601 needs to be adapted to pump the prefilling fluid 650 initially present in the bottles 102. The pump 601 may be a vacuum pump in case the prefilling fluid 650 is a gas, or a liquid pump, in case the prefilling fluid 650 is a liquid. Such pump 601 may use any pumping technology known in the art, such as, with no limitation: membrane pump, peristaltic pump, piston pump, centrifugal pump, positive displacement pump, etc. The pump 601 may be uni-directional (configured to move fluid away from the bottles), or bi-directional (capable to move fluid in either direction).

FIG. 6*b* shows a sampling device 650 with the fluid inlet ports 614 of the different sampling bottles 102 connected to a fluid manifold 603, allowing each sample to be acquired from the fluid line 604 within said manifold 603, in accordance with an embodiment of the invention. Illustratively, all samples may enter the manifold 603 through a common inlet 605. The bottle 102 connected to the last outlet of the manifold 603 may be used to sample a small amount of fluid prior to sampling into the other bottles. This allows to effectively flush the fluid line 604, and to ensure that samples acquired in the other bottles are free of contamination from stagnant fluid present in the fluid line 604.

In FIG. 6*b*, the fluid inlet ports 614 of the different sampling bottles 102 are shown connected to a fluid manifold 603, allowing each sample to be acquired from the fluid line 604 within said manifold. All samples enter the manifold 603 through a common inlet 605. The bottle 606 connected to the last outlet of the manifold 603 may be used to sample a small amount of fluid prior to sampling into the other bottles. This allows to effectively flush the fluid line 604, and to ensure that samples acquired in the other bottles are free of contamination from stagnant fluid present in the fluid line 604.

Figure 7:
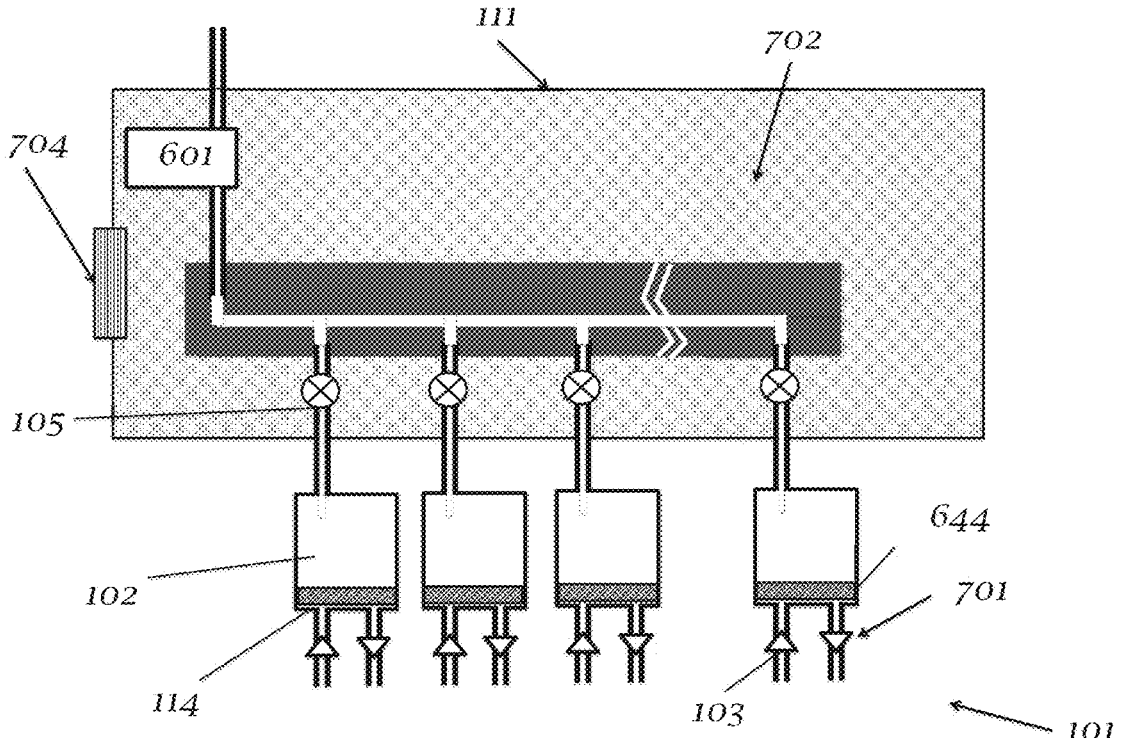
FIG. 7 shows sample bottles that include a third connection, in accordance with an embodiment of the invention.

FIG. 7 shows sample bottles 102 that include a third connection 701, in accordance with an embodiment of the invention. The third connection 701, called a flush port, may be located on the same side of the piston 644 as the fluid inlet port 614, and which is fitted with a flush valve allowing sampling fluid to exit the bottle but preventing it from traveling in the opposite direction. Such flush port 701 may include, without limitation, a check valve, one-way valve, a ball and spring arrangement, a flexible membrane, a back-pressure regulator, or may have any other construction that allows a similar function to be performed. By repeatedly operating the pump 601 so as to initially pull sampling fluid into the bottle 102 through the fluid inlet port 614, and then in opposite direction to expel the sampled fluid out of the bottle through the flush port 701, the inside of the sampling bottle 102 can be effectively flushed, thus reducing the amount of possible sample contamination and improving its representativeness. It is preferable, in this type of operation, to ensure that the fluid exiting the pump port connected to the outside of the pumping module, as well as the fluid exiting from the flush ports of the different bottles, is guided (using tubing, piping, or any other type of conduit known in the art) to an area where it cannot interact with, or contaminate, the sampling medium.

Figure 3:
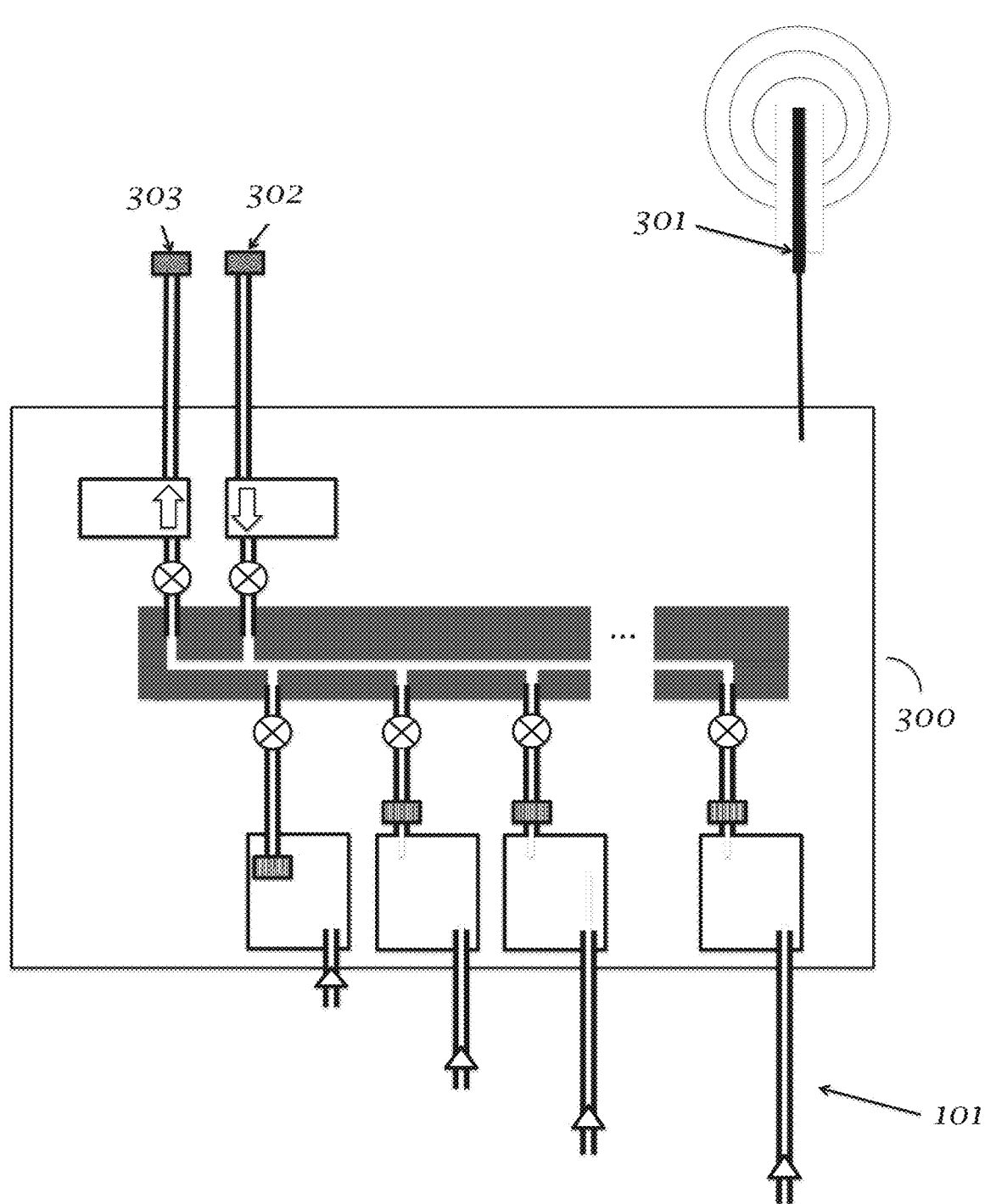
FIG. 3 shows an exemplary application in which the entire sampling device is submersed, in accordance with an embodiment of the invention.

In various embodiments, the fluid inlet port 114 of each bottle 102 may be connected, either directly or using sampling tubing, piping or any other type of fluidic conduit known to the person skilled in the art, to an inlet valve, and then further to the medium 101 to be sampled. Such an inlet valve 103 may allow fluid to enter into the bottle 102 once the pressure across the valve 103 reaches a certain level, called the valve's cracking pressure. Such an inlet valve 103 may consist, with no limitation, of a check valve, one-way valve, a ball and spring arrangement, a flexible membrane, a backpressure regulator, or may have any other construction that allows a similar function to be performed. The inlet valve 103 may also act as a directional or one-way check valve, blocking fluid and gases from traveling in the direction from the bottle outwards. The inlet valve 103 may also play the role of isolating the sample from the sampling medium 101 after sample acquisition. The sampling tubing connecting each bottle to the corresponding inlet valve may have different lengths, and may extend either to different locations, or to different depths in the medium to be sampled (as shown in FIGS. 2 and 3). Alternatively, the sampling tubing may be positioned close to the water surface. As already mentioned, the fluid inlet port 114 may be connected to a pipe, to tubing, or to any other conduit containing or circulating the fluid to be sampled (see FIG. 4). Advantageously, the fluid inlet ports 114 and/or the corresponding inlet valves 103 may be positioned in such a way as to minimize the amount of dead volume contained between the said check valves 103 and the representative portion of the fluid 101 to be sampled.

A sampling bottle 102 may also incorporate an inlet filter 211, as shown in FIG. 2, between the fluid inlet port 114 and the sampling medium 101. Such a filter 211 may be a physical filter used to retain particulate matter above a certain size, or it could be a chemical filter, which retains certain chemical components, depending on properties such as, with no limitation: polarity, structure, hydrophobicity, molecular weight, presence of certain radicals. Such a filter 211 may include, for example, a solid phase extraction filter or column, a filter that collects and concentrates radioactive material, a biological filter, an absorbent medium, a scavenging medium, a pre-concentration device, a gas chromatography preconcentrator, a hydrophobic filter, a hydrophilic filter, a size-exclusion filter or column, a mechanical filter, a sieve, a porous membrane, a frit, a sponge, a hydrocarbon filter, a separation column, an activated carbon filter, or any other type of filter or separation device known in the art as well as possible combinations thereof. The filter 211 may be collected during bottle retrieval and further analyzed.

Each bottle 102 may be at least partially pre-filled with a product such as, with no limitation: a chemical reagent, an absorption medium, a biocide, a fixing agent, a biological reagent, a culture medium, or a combination thereof whereas the sample, when entering the bottle 102, comes into contact and/or mixes with said product.

Each bottle 102 may be outfitted with a sensor for confirming that the bottle filling operation is being correctly performed. Such a sensor may consist of a temperature probe, a conductivity probe, an electrochemical sensor, an optical sensor, a magnetic sensor for detecting piston movement, a reed switch, a density probe, a physical measurement, a force measurement, a deflection measurement, a chemical measurement, a biological or biochemical measurement, or any other type of sensor or combination thereof known to the person skilled in the art and that is capable to detect presence of the sampling fluid in the bottle.

It is apparent that the described sampling device avoids the cross-contamination issues that are inherent in other sampling systems: by using a unique fluid inlet port and sampling tubing per bottle, each sample is collected completely independently from the previous and subsequent samples, fluid from each sample only entering in contact with the components of the corresponding sampling bottle.

In various embodiments, the sampling device may be separated from the sampling medium (see FIGS. 4 and 5) or it may be partially (see FIGS. 1 and 2) or totally submersed (see FIG. 3). In case of partial or total submersion, the pumping module housing 111 may be watertight so as to protect the control electronics from inadvertent water contact. Optional pump exhaust modules 110 and 112 as well as an optional communication antenna 301 (see FIG. 3) may be extended to a location above the water level.

In addition to being watertight, the pumping module housing 111 also needs to be able to withstand the hydrostatic pressure at the depth where the sampling device is deployed, in case of total immersion. This could be accomplished by using materials and a mechanical design that ensures sufficient mechanical strength to resist the mechanical stress imparted by the hydrostatic pressure, or by using a pressure-balanced approach, whereby the interior of the pumping module 111 is completely filled with a pressure-balancing fluid 702, as shown in FIG. 7 (such as, for example and with no limitations, a non-conductive mineral oil, silicone oil, fluorinated oil or similar material) that is at substantially the same pressure as the sampling medium. In order to account for shrinkage and compression as the device is deployed at depth, a pressure compensation module 704 that may include a system of bellows, or a diaphragm, or any other pressure compensation technique known in the art, may be used to equalize the pressure of the pressure-balancing fluid with that of the sampling medium (see FIG. 7). Once such pressures are equalized, the forces acting on the different mechanical elements are greatly diminished, and the need for mechanical strength is reduced. Such pressure-balancing approaches are commonly used in the subsea and oceanography industry, in order to reduce the size and weight of pressure housings for electronics modules or motors, and the person skilled in the art will recognize that many techniques are known for realizing a pressure-balanced device.

In addition to the pumping module section requirement to withstand hydrostatic pressures at depth, the sampling bottles 102 and tubes also need to be designed with sufficient mechanical strength to resist the mechanical stress imparted by the hydrostatic pressure, when not used in pressure-balanced configuration. Illustratively, in the case that the sample bottles 102 and tubes are pressure balanced, they will be prefilled with fluid on the pump side of the piston 644 (see FIG. 6*a*), while the inlet side of the piston 644 may be prefilled with deionized water, saline water, fixing agent, biocide or any combination of thereof.

The pumping module housing 111 or the additional protection housing may also be outfitted with buoyancy elements 210, as shown in FIG. 2, that are made of materials or composites that are less dense than water, such as (and with no limitation): closed-cell foam, syntactic foam bricks, air-filled pockets or components, certain plastics or wood. These buoyancy elements 210 should provide sufficient buoyancy to allow the sampling device to float in the sampling medium 101. An additional weight may also be added as ballast, to keep the sampling device in a desired orientation while floating, such as in upright orientation, for example. Many different ways to achieve balance and orientation of a floating device in a body of water or other fluid exist and are known to the person skilled in the art.

Examples of Deployment and Operation of the Sampling Device

Several types of possible deployment and operation of a sampling device are described below. It is to be understood that the following deployments and operation of the sampling device are exemplary, and not meant to be limiting.

In a first application example, shown in FIG. 1, the device is deployed near a liquid sampling medium to collect samples near the surface of the sampling medium 101. The pumping module 111 is positioned outside the sampling medium, whereas the bottles 102 may be submersed in the sampling medium 101 so their inlet ports 114 are at the desired sampling depth. When a sample acquisition is requested, the electronics control module instructs the control valve 105 corresponding to the selected sampling bottle to open, and activates the vacuum pump 109. As the pump starts removing air from the bottle via the manifold 107 and pumping tube 108, and also through the optional pumping filter 104, the pressure in the bottle 102 starts to drop, and the corresponding differential pressure across the bottle's inlet valve 103 increases. The air from the pump 109 is exhausted through an exhaust filter 112, optionally attached to the pump through a tube 110. Once this pressure difference reaches the inlet valve's cracking pressure, the inlet valve 103 allows water to pass through, thus filling the recipient 102.

The total sampled volume may be controlled by the amount of time that the vacuum pump 109 is activated, and by the pressure drop created by the vacuum pump 109 during operation. To allow better pumping control, the control electronics may also be connected to a pressure sensor, which may read the pressure at the low-pressure port of the vacuum pump or, alternatively, inside the vacuum manifold. The control electronics may also include a second sensor that measures depth where the sampling is performed. Alternatively, the sampling depth may be supplied to the control electronics by means of an external command or of a configuration parameter.

The control electronics may activate the vacuum pump 109 for short periods of time to acquire just a small amount of fluid each time. The control electronics may adjust the amount of time the pump 109 is activated based on a combination of information from the pressure sensor, depth sensor, or known sampling depth, so as to control accurately the amount of sample acquired at each sampling operation. This may be repeated at time intervals, the sampled amounts each time being added to the sampling bottle 102 to create a composite sample. A typical application can be the acquisition of a 24-hour composite sample. Another application can be the acquisition of flow-proportional samples, whereas the control electronics samples small increments of fluid at a frequency or rate that is proportional to the reading of a flow rate or flow velocity sensor.

In various embodiments, the control electronics may activate the pump 109 for sufficient time to acquire a single grab sample, which partially or completely fills the recipient. The timing of the pump 109 may be controlled such as to collect the exact desired sample volume.

The pumping filter may be installed outside the bottle (pumping filter 104), or inside the bottle (pumping filter 106). By installing the pumping filter 106 within the bottle, the total sampled volume may be controlled by the position of the pumping filter. Upon activation of the vacuum pump, the raising fluid level in the bottle will reach, after a certain pumping time T, the level where the pumping filter 106 is installed. Once filled with fluid, the flow through the pumping filter 106 will stop, which will effectively stop the pumping action. The fluid level may continue to rise slightly, until the pressure in the bottle 102 becomes insufficient to overcome the inlet valve's cracking pressure, at which time fluid flow into the bottle 102 will stop. This method would allow control over the fluid volume regardless of the depth where sampling is performed. The pumping filter 106 can be extended into the bottle through a nozzle or tubing 113, which allows further control on the sampling volume.

In the cases described above, the sampling depth is typically limited by the cracking pressure of the inlet valves 103 used: indeed, if the difference between the hydrostatic pressure of the sampling medium 101 and the pressure inside a bottle 102 overcomes the cracking pressure of the corresponding inlet valve 103, the sampling medium 101 will enter the bottle 102 and start filling it until the inlet valve 103 closes again.

The bottles 102 may also be located outside the liquid sampling medium 101, in which case their fluid inlet ports 114 may be connected with tubing to the sampling medium 101, at the desired sampling depth. Such sampling requires suction of the samples from the sampling medium, through the connecting tubing, and into the bottles 102; the height at which the bottles 102 can be located above the liquid fluid level is limited therefore on one hand by the pump performance (its ability to produce sufficient vacuum), and on the other hand by the maximum fluid column height that can be pulled without producing cavitation.

In a second exemplary application, sampling at depth is accomplished by connecting the water inlet port 114 of each bottle 102 to tubing 202 that reaches to the desired depth. Illustratively, each bottle 102 may be configured to sample at a different depth 201 (shown FIG. 2), or all bottles may sample at the same depth. An optional inlet filter 211 may be placed on the inlet tubing to a bottle 102. The inlet valves 103 may be placed at the bottle level, or could be placed at depth as well. The latter placement, as shown in FIG. 2, limits access of the sampling medium 101 to the sampling tubing 202 until the sampling operation has started, thus limiting or eliminating contamination by fluid contained in the tubing 202 which would not be representative of the sampling medium at the moment of sampling. In order to ensure that the difference between the hydrostatic pressure of the sampling medium 101 and the pressure inside the bottles 102 does not overcome the cracking pressure of the inlet valves 103, the bottles 102 may be pressurized prior to deployment. Such pressurization may be performed manually (for example, by injecting pressurized air through the inlet valve 103 of each bottle 102, said air being at a pressure similar to the hydrostatic pressure where sampling is intended), using a hand pump, a compressor, a pressurized air canister (or other gas), a pressurized line, a pressure regulator, or any other means known in the art. In other embodiments, and conveniently, the sampling device may include, in addition to the vacuum pump 205, a second pump 204, called "pressure pump", whose role is to achieve said pressurization prior to deployment. In this case, the vacuum pump's low pressure connection, and the pressure pump's high pressure connection may be connected using master valves 206, 207 to the manifold. The exhaust of the pumps 204 and 205 may also be connected, by tubing, piping, or other types of connection, to the outside of the pumping housing, and to optional pump exhaust modules 208 and 209. Both the pressure 204 and the vacuum 205 pump may use the same exhaust module, as long as it allows passage of gas in both directions (such as, for example, a dry hydrophobic membrane).

When pressurization of a given bottle 102 is desired, the master valve 206 corresponding to the pressure pump 204 as well as the control valve 105 corresponding to the bottle 102 are opened, the master valve 207 corresponding to the vacuum pump 205 is closed, and the pressure pump 204 is operated. This will pump air into the bottle 102, thus increasing the pressure. Of course, all control valves 105 could be opened simultaneously for simultaneous pressurization of all the bottles 102. After a certain pumping time, or when a pre-defined pressure has been reached, the valves are closed and the pump 204 is stopped. It is understood that, in order to achieve and maintain pressurization, the bottles' inlet valves 103 will need to operate as check valves, keeping the pressurized gas inside the bottles 102. It is again understood that a pressure sensor may be used to measure pressure inside the pumping manifold, or at the exit of the pressure pump, so as to control the pressure applied to the bottles.

FIG. 3 shows an exemplary third application in which the entire sampling device 300 may be submersed, in accordance with an embodiment of the invention. This may be required, for example, if the device 300 needs to be hidden from view, or it needs to perform sampling at depth and using tubing may be impractical. In this case, in addition to the features described above, the sampling device 300 may have its pump exhaust modules 302 and 303 and antenna 301 extended to the surface of the sampling medium 101, so as to allow pumping and communication. The necessary tubing and antenna cables may be separate or integrated in a single cable, and may extend to a shore or be attached to an optional buoy. Said buoy may also support some of the sampling device's underwater weight by providing buoyancy for maintaining the sampling device at the desired depth. Said buoy may also act as a signaling buoy for marking the position of the sampling device 300, and may be outfitted with lights, radio beacons or other means of signaling its position. It may also be outfitted with a GPS antenna or device for communicating its position.

Figure 4:
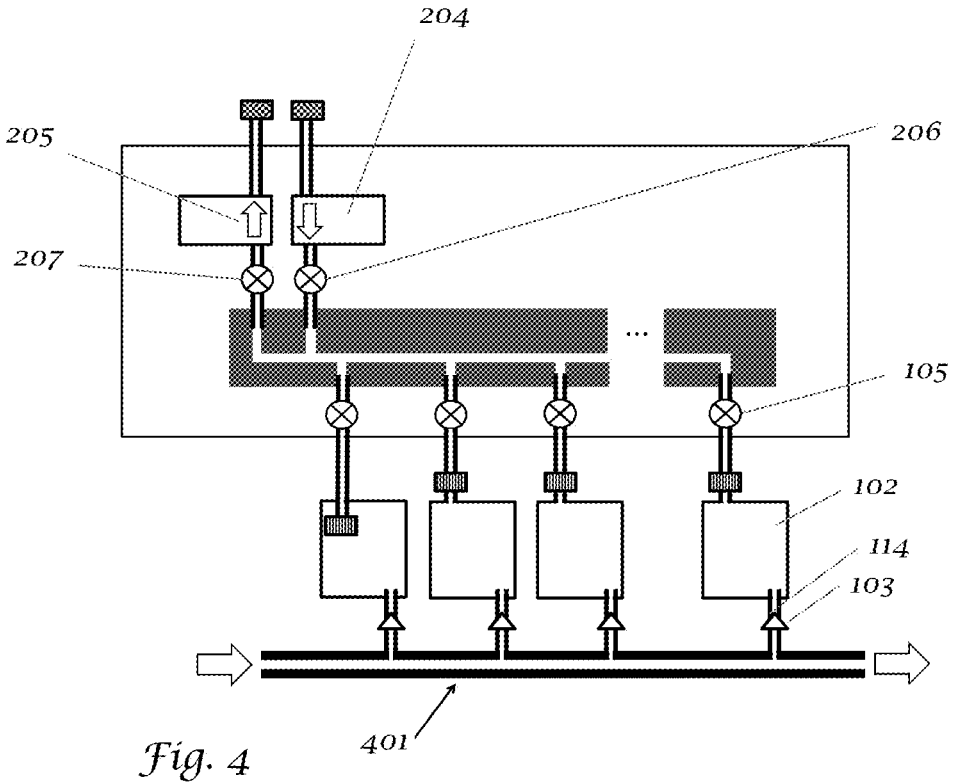
FIG. 4 shows an exemplary application in which sampling is performed from a closed conduit circulating the fluid of interest, in accordance with an embodiment of the invention.

FIG. 4 shows an exemplary fourth application in which sampling needs to be performed from a closed conduit 401 circulating the fluid of interest, such as, without limitation, a pipe, a length of tubing, and/or a manifold, in accordance with an embodiment of the invention. The conduit 401 may be, for example, a drinking water pipe, or an industrial process water pipe. In this case, the different bottle's fluid inlets 114 are connected to the conduit 401 either through individual tubing, or through a manifold. Ideally, the inlet valves 103 are positioned as close as possible to the conduit 401 circulating the fluid of interest, so as to avoid stagnant fluid between the inlet valves 103 and the conduit 401. The cracking pressure of the inlet valves 103, as well as the optional pre-pressurization of the bottles 102, need to be adjusted such that, at the operating pressure inside the conduit 401, fluid of interest cannot enter the sampling bottle 102. When a sample needs to be acquired in a specific bottle 102, the (optional) master valve 207 corresponding to the vacuum pump 205 and the corresponding control valve 105 corresponding to the selected bottle 201 are opened by the control electronics, and the vacuum pump 205 operated. By lowering the pressure inside the selected bottle 102, eventually the pressure difference across the inlet valve 103 overcomes the cracking pressure of the inlet valve 103, and fluid starts to fill the bottle 102.

In a fifth application example, sampling of the water column in areas affected by oil spills can be achieved using a sampling device similar to the one shown in FIG. 2. Such a device could be installed in an oil spill area prior to applying any surfactant treatment to the spill. It may be buoyant, and may contain a communication antenna, GPS location capability as well as signaling lights and/or radio beacons. It may also contain different types of sensors, such as (for example) fluorescence probes, turbidity probes, pH sensors etc., located at different depths. The sampling tubes may extend to different depths, so as to sample different portions of the water column at the location of the sampling device. Whenever triggered by an external command received through the communication antenna, by a preprogrammed sample alert, or when triggered by measurements from the external sensors, the control electronics would then initiate the acquisition of one or multiple samples, at one or multiple depths. The sampling device may also communicate its GPS position and/or the external sensor readings, either periodically or when interrogated via the communication antenna. Communication may be achieved through GSM, 3G, 4G, LTE or similar cell phone networks and protocols, or by a radio link such as LoRa, LoRaWAN, Sigfox, or by any other means of remote communication. The devices may be attached to existing fixed infrastructure, to existing buoys, or they may be drifting. Upon completion of the sampling program, the devices may be located using their known location or transmitted GPS coordinates, and retrieved along with the physical samples. Deployment of multiple such devices throughout an oil spill area would allow data and physical sample collection throughout a spill event, from initial detection of the spill and throughout the treatment process. In addition to monitoring spills and accidental releases, such devices could also be used to monitor natural seeps; to collect baseline data about sea water quality prior to drilling operations; to monitor for pollution during drilling and casing operations; for long term operational monitoring throughout the production phase; for monitoring during and after the decommissioning phase.

In a further application example, sampling needs to be performed at depth. Such could be case in the ocean, for example. The sampling device 700 presented in FIG. 7 may be used, where the pump 601 may be a peristaltic pump, and the pumping module housing 111 could be deployed in a pressure-balanced configuration, in accordance with an embodiment of the invention. Pressure-balancing could be achieved by filling the interior of the pumping module housing 111 with a pressure equalization fluid 702 that is compatible with all the materials and electrical or electronic components present in the housing, and providing a pressure equalization mechanism 704 that allows the pressure of the sampling medium fluid 101 to be transmitted to the pressure equalization fluid 702, without allowing the possibility of it mixing with the sampling fluid 101. Such pressure equalization mechanism could be, without any limitation, one of a sealed moving part like a piston, a membrane, a bag, a bladder, bellows, or any other similar mechanism known in the art.

Initially the sampling pistons 644 are located near the inlet ports 114 of the bottles 102, and the portions of the bottles 102 opposite to the inlet ports 114 are prefilled with a prefilling fluid, which may, in this example, be water (either fresh or sea water). When a sample needs to be collected in a specific bottle 102, for example, the corresponding control valve 105 is opened, the peristaltic pump is actuated to pull a certain volume of the prefilling fluid out of the bottle, which in turn pulls the piston 644 into the bottle. An equal amount of sampling fluid is retrieved at the same time into the bottle 102 through the inlet port 114.

The exhaust port of the pump 601 needs to be positioned (or extended with tubing) so as to minimize possible contamination of the medium to be sampled with the pre-filling fluid initially present in the bottle 102. The peristaltic pump 601 may then be actuated to push into the bottle 102, which then pushes the piston 644 and flushes the previously retrieved sampling fluid through the bottle's flush port 701. This operation may be repeated for several cycles to fully flush the interior of the sample bottle and thus ensure that any contamination that may have been present in the bottles or sampling tubes and valves is minimized. After a number of flushing cycles, the pump 601 is operated so as to fill the bottle 102 with sampling fluid one last time, then the pump 601 is stopped and the control valve 105 is closed. This operating mode allows sampling to be performed at depth, and in such a way that the total weight of the device does not change (which would have been the case if a previously empty container had been filled with sampling fluid). This aspect is particularly important and well adapted to sampling off buoyancy-driven underwater gliders and autonomous underwater vehicles where maintaining constant buoyancy of the vehicle throughout and subsequent to the sample acquisition process is essential.

Alternatively, the small volume between the inlet port 114 and the piston 644 is prefilled with a fixing agent or biocide.

This may be required in some cases where it is desired to halt the microbial, chemical or algal evolution within the sample.

By operating the pump for short periods of time, so as to acquire a well-defined volume of sampling fluid each time, either at equally spaced intervals or at a rate that is proportional to the reading of a flow rate or flow velocity sensor, it is possible to obtain composite or, respectively, flow-proportional samples.

Sample Treatment and Measurement

Further embodiments of the invention allow the acquired samples to be processed and monitored within the sampling device, so as to measure certain properties of the acquired samples.

Reagent mixing: The sample is acquired in a sampling bottle by a sampling device as described above. The sampling bottle may be pre-loaded with a reagent, so that as the sample is acquired, it mixes with the reagent. The reagent may be in solid form, or in liquid form, however it is understood that mixing with a liquid reagent could be faster and more effective. The reagent may be a fixing agent, a chemical reagent, a bio-reagent, a cell culture or growth medium, or a combination thereof. The reagent may for example contain a growth medium specific to a certain strain or type of bacteria, as well as chemical species that could be modified by the metabolism of such bacteria. Such modifications may result in a change of the observable properties of the sample, such as a change in color, appearance of fluorescence, development of turbidity, a change in pH or conductivity, a change in other sample properties, or a combination thereof. The sampling bottle may be preloaded with a combination of multiple reagents of different types.

In one example, the reagent may contain a growth medium, as well as the chemical MUG (4-methylumbelliferyl-β-D-glucuronide). *Escherichia Coli* (*E. Coli*) bacteria contain an enzyme (β-glucuronidase) which hydrolyzes MUG and transforms it into MUF (4-methylumbelliferyl), which is fluorescent. The presence of this fluorescent compound can be an indicator of presence of *E. Coli* bacteria. In another example, the reagent may contain a growth medium, as well as the chemical ONPG (ortho-nitrophenyl-β-galactoside). Coliform bacteria hydrolyze ONPG and transform it into ONP (ortho-nitrophenol), which has a characteristic yellow color. The presence of this chromogenic compound can be an indicator of presence of Coliform bacteria in general. In yet another example, the reagent may contain both MUG and ONPG.

Figure 8:
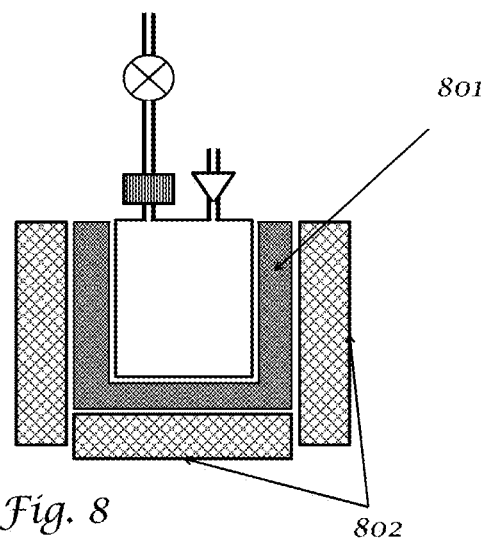
FIG. 8 shows a sampling bottle that includes or is in contact with a temperature control apparatus 801, in accordance with an embodiment of the invention.

Temperature control (incubation): FIG. 8 shows a sampling bottle that includes or is in contact with a temperature control apparatus 801, in accordance with an embodiment of the invention. The temperature control apparatus 801 may be a heating apparatus, a cooling apparatus, or may perform both heating and cooling functions. The temperature control apparatus 801 may include a resistive heater located inside the bottle; it could be a microwave generator or an infrared light source, located in proximity of the bottle; a convection heater; an oven or equivalent; it could be a heating strip or heating sleeve surrounding the bottle; a heating block; a Peltier device; a heat pump; or any other type of heating device known in the art, as well as combinations thereof. The temperature control apparatus 801, or the sample bottle, may further include a transducer that measures the temperature, such as a resistive temperature detector (RTD), a thermocouple, a thermistor, a temperature sensor contained within an integrated circuit, or any other type of temperature measurement device known in the art. The temperature control apparatus 801, as well as the temperature transducer, may be operated by the control electronics, which can then modulate the amount of heating power produced by the heating apparatus or the amount of heat removed by the cooling apparatus, so as to control the bottle temperature accurately. Different types of algorithms are known in the art for accurately controlling a process parameter such as the temperature of the temperature control apparatus or of the sample bottle, including but not limited to: on-off control, proportional control, PID control as well as any combinations thereof. A battery or other power source contained within the device may power the temperature control apparatus. The temperature control apparatus may include or be surrounded by a thermal isolation layer 802, to limit heat exchange with the environment and thus reduce power consumption. The temperature control apparatus 801 may apply different temperature profiles to the sample. For example, it may heat or cool the sample initially to a first temperature $T_1$ for a duration $t_1$, then further heat or cool the sample to a temperature $T_2$ for a duration $t_2$, and so on. The temperature control apparatus may also apply controlled temperature ramps, whereas the temperature is increased or decreased at a controlled rate.

It is understood that each bottle may be in contact with an individual temperature control apparatus, or that all bottles may be in contact with a unique temperature control apparatus. The temperature control apparatus may be maintained at a fixed temperature (conventional temperature control), or more complex temperature profiles may be imposed. In the case of a device requiring battery operation, it may be preferred to have an individual temperature control apparatus for each bottle, which allows independent control of the bottles' temperatures. This greatly minimizes the required power, since heating is only applied to the bottles that require temperature control and not to the totality of the bottles. Further, this allows different bottles to be heated differently, so as, for example, to maintain them at different temperatures, or to impose different temperature ramps to each sample.

Figure 9:
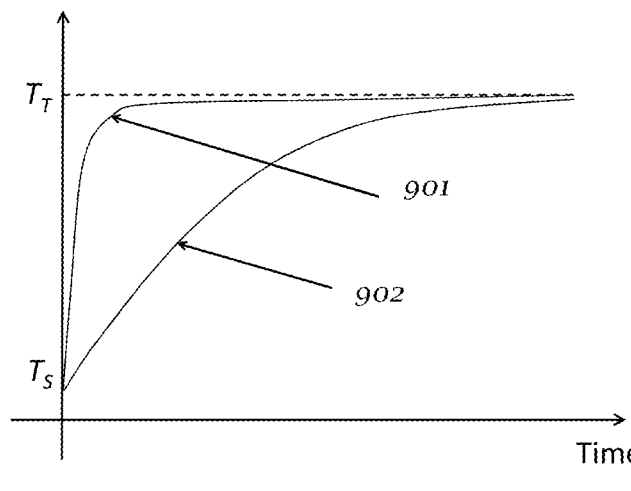
FIG. 9 graphically shows a time versus temperature chart of various temperature control algorithms, in accordance with an embodiment of the invention.

Smart temperature control: In certain applications, it may be important to bring the sample to a desired target temperature as soon as possible after sample acquisition into the bottle. FIG. 9 graphically shows a time versus temperature chart of various temperature control algorithms, in accordance with an embodiment of the invention. By using conventional temperature control, which consists of maintaining the temperature of the temperature control apparatus at the target temperature, the sample would reach the target temperature asymptotically, in a relatively long time-curve 902. In order to shorten the time required for the sample to reach the target temperature-curve 901, the temperature control apparatus may incorporate a smart temperature control algorithm.

For example, in embodiments where heating of the sample is desired and the temperature control apparatus consists of a heating apparatus, the smart temperature control algorithm may initially inject a larger amount of heat (at sampling time) in order to rapidly bring the sample to the target temperature, and then maintain that temperature constant with no temperature overshoot—curve 901. Such algorithm could calculate and then inject the exact amount of initial heat that is needed to heat the sample to the target temperature, basing its calculation on knowledge of the initial temperature of the heating block and of the bottle, knowledge of the amount of fluid to be sampled and of its temperature and thermal properties, knowledge of the mechanical and thermal properties of all the materials involved in the construction of the heating apparatus and of the sample bottle, or a combination of such information.

Considering $T_S$ and $T_H$ the initial temperatures of the sampling medium prior to sampling, and of the heating apparatus and sample bottle assembly, respectively, and $T_T$ the desired target temperature that needs to be reached, and considering the heat capacities of the acquired sample, $C_S$, and of the heating apparatus and sample bottle assembly, $C_H$, it is possible to deduce the total amount of energy E that needs to be injected into the heating block in order to raise the temperature of the sample, bottle and heating block to the desired target temperature $T_T$:

$$E=C_H\times(T_T-T_H)+C_S\times(T_T-T_S).$$

Depending on the type of heating device used, the amount of energy E that needs to be injected may be generated by different means, and that translates in different means for activating the heater. For example, if we consider a heating device consisting of a resistive heater of resistance R, and that the energy E is injected by applying a DC voltage V to the heating device for a certain amount of time t, the time t can be calculated from $t=E\times R/V^2$.

Injecting the heat E rapidly into the heating apparatus may lead to an overshoot in the temperature of the heating apparatus, but not in the temperature of the sample, since the exact amount of required heat is initially injected, and heat always flows from the warmer to the colder body, in this case from the heating device to the bottle, and then to the sample. Once the temperature of the heating apparatus drops to $T_T$ again, after the initial injection of heat E, the fluid sample, sample bottle and heating device are equilibrated in temperature, and conventional temperature control may be resumed to maintain the heating apparatus temperature constant at the $T_T$ value.

The person skilled in the art will acknowledge that $C_H$ and $C_S$ introduced above may either be measured using conventional calorimetric equipment, or may be calculated from knowledge of the different materials involved, as well as their weights and specific heats. For example, if the sampling medium is a fluid that has specific heat $c_S$, density d, and the total volume sampled is V, then the heat capacity of the sample may be calculated as $C_S=c_S\times d\times V$.

It is understood that the above example provides only one possible implementation of a smart temperature control algorithm. It is further understood that additional corrections for factors such as heat loss through conduction, convection and radiation, for different initial temperatures of the heating block and sample bottle, or for different geometries of the sampling bottle and heating apparatus, may be included in the above formula to improve its accuracy. It is also understood that, while the above example relates to the case of heating a sample using a heating apparatus, the same smart temperature control algorithm can be used for cooling a sample using a cooling apparatus, in which case E represents the amount of energy that needs to be removed by the temperature control apparatus.

Measurement of certain sample properties may critically depend on the temperature history of the sample. For example, quantification of initial bacterial content within a sample may be based on measuring the required incubation time $t_1$ at a certain target temperature $T_T$ before certain observable effects may occur. Such observable effect could be, for example, appearance of fluorescence or absorbance due to presence of certain compounds produced by enzymatic reactions. By using conventional temperature control, the temperature of the sample would asymptotically approach the target temperature $T_T$, in a time that is relatively long and that depends on a number of parameters such as the initial sample temperature, and the total volume sampled. By implementing the smart temperature control algorithm outlined above, heating from the sampling medium temperature $T_S$ to the target temperature $T_T$ may advantageously be performed faster and in a well-controlled fashion, since the exact amount of required heat is injected or removed at sampling time. This will result in a much more reproducible incubation time $t_1$, which will in turn lead to more accurate quantification results.

For example, for wild *Escherichia Coli* (*E. Coli*) bacterial strains, the doubling time in an appropriate growth medium at 37 degrees Celsius is known to be between 20 and 30 minutes. A factor of 2 error in quantification may therefore be introduced by an error of 20 to 30 minutes in measuring the incubation time. This example illustrates clearly the importance of implementing the smart temperature control algorithm outlined above, which allows more accurate and faster temperature control.

Figure 10:
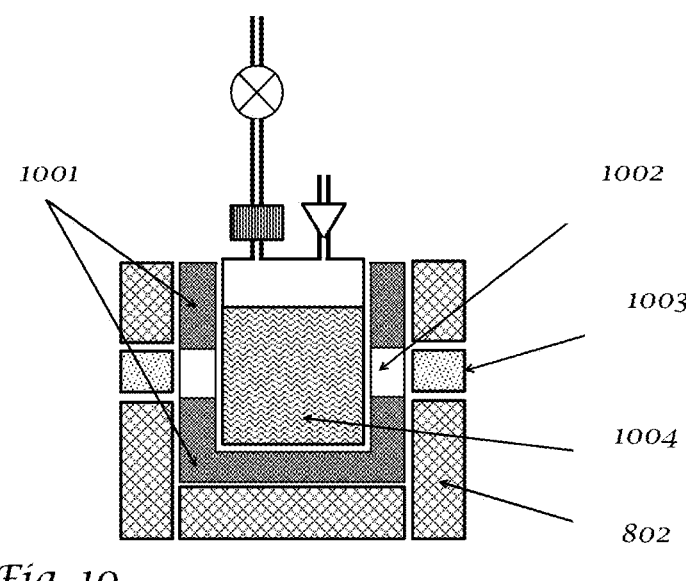
FIG. 10 shows the sample bottle outfitted with an optical sensor, in accordance with an embodiment of the invention.

Optical measurements: FIG. 10 shows the sample bottle outfitted with an optical sensor 1003, in accordance with an embodiment of the invention. The optical sensor 1003 may be capable of measuring different optical properties of the sample, such as color change, absorbance at specific wavelengths, turbidity, fluorescence, birefringence, or any other type of optical measurement known in the art. Such optical sensor may measure different optical properties of the sample located in the sample bottle by sending light into the bottle using one or multiple light sources, and measuring the intensity of the light using one or multiple light detectors. Light sources may consist of incandescent sources, halogen lamps, gas discharge lamps, light emitting diodes, laser diodes or other types of laser sources, and any other type of light source known in the art. Light detectors may consist of photodiodes; phototransistors; cascade-effect photodiodes; photoamplifiers; CMOS sensors; CCD sensors; spectrometers; pyroelectric detectors; bolometers; and any other devices known in the art and capable to measure or quantify light intensity, as well as all combinations and arrays or matrices of such devices. Such light sources and light detectors may be used directly, or they may be coupled to optical waveguides, optical fibers, liquid waveguides, light channel, or any other kinds of light-guiding components known in the art as well as any combinations thereof. The light sources and light detectors may be used alone, or coupled to other types of optical components such as optical filters; neutral density filters; interference filters; quarter wave plates; polarizers; low-pass; band-pass or high-pass optical filters; mirrors; monochromators; collimators; gratings, including diffraction gratings; apertures; lenses; any other types of active or passive optical devices known in the art, as well as any combinations thereof.

The optical sensor 1003 may be controlled by, or communicate its values to a computing unit, which contains a form of memory for storing the measurements. Such computing unit could be a microprocessor, a microcontroller, a desktop or laptop computer, a smart phone, a smart watch, a tablet, a single-board computer, or any other type of device capable to record and process the measurements produced by the optical sensor 1003.

The optical sensor may be used together with the temperature control apparatus, or separately. In one embodiment, as shown in FIG. 10, the optical sensor 1003 is positioned around the bottle and temperature control apparatus 1001, whereas the light sources and light detectors are aligned with openings 1002 (optical windows) provided in the temperature control apparatus, to allow light to travel from the light source to the bottle, across the collected sample 1004 within the bottle, and to the light detector.

Figure 11:
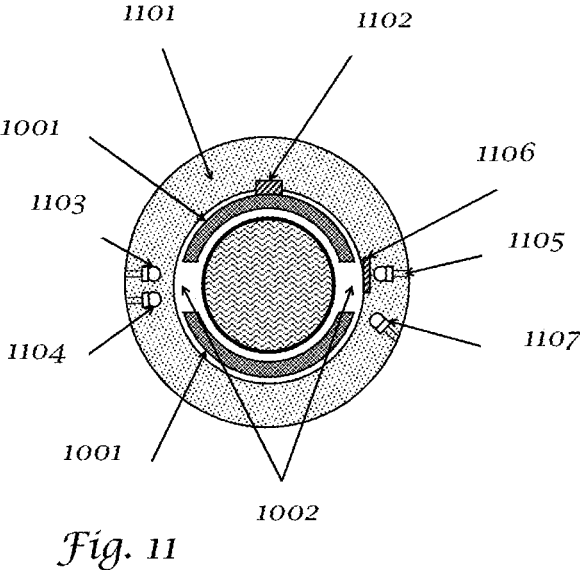
FIG. 11 shows a top view of an optical sensor having the shape of a sensor ring, in accordance with an embodiment of the invention.

FIG. 11 shows a top view of an optical sensor having the shape of a sensor ring 1101, in accordance with an embodiment of the invention. The light sources 1103, 1104, 1107 on such an optical sensor may be monochromatic LED's, and the light detector may be a photodiode 1105. LED's 1103, 1104 for measuring absorbance of the sample at specific wavelengths may be placed in a position that is opposite to the photodiode 1105. LED's 1103 and 1104 may be chosen to operate at wavelengths that allow detecting a specific coloring of the sample independent of the sample becoming turbid due, for example, to bacterial growth. LED's 1107 for exciting fluorescence may be positioned such that the light from the LED reaches the bottle in the proximity of the photodiode 1105, but at such an angle that reflected light does not reach the photodiode 1105. The LED's 1103, 1104, 1107 and the photodiode 1105 may be aligned with openings in the temperature control apparatus (optical windows). The photodiode 1105 may be outfitted with an optical filter 1106 that blocks the fluorescence excitation wavelength, while allowing passage of the emitted fluorescence signal as well as the light from the other LED's. Optionally, the optical sensor may also be outfitted with a temperature sensor 1102, to measure the temperature of different optical components, or that of the temperature control apparatus.

The optical sensor may include two LED's 1103, 1104 positioned opposite to the photodiode 1105. One such LED may emit light at a wavelength where the sample, or of a reagent mixed with the sample, absorbs light, whereas the second LED may emit light at a wavelength where the sample or reagent do not absorb. The LED's 1103, 1104 may be positioned such that the light from the LED's 1103, 1104 to the photodiode 1105 follow similar optical paths. In this case, scattering due to sample turbidity will affect the light from both LED's 1103, 1104 similarly, whereas absorbance will affect light from the first LED only. By measuring light from both LED's 1103, 1104, it is therefore possible to correct for any light scattering due to sample turbidity, and thus have an accurate measurement of absorbance with no artifact or influence from turbidity.

The optical sensor may be positioned at the bottom of the bottle, such as to measure through the bottom of the bottle. However, such a measurement may be affected by deposits from the sample, which tend to aggregate at the bottom. In a preferred arrangement, the optical sensor is positioned at the midway height of the sample in the bottle. This allows for accurate measurements to be performed without any influence from bottom deposits.

Figure 12:
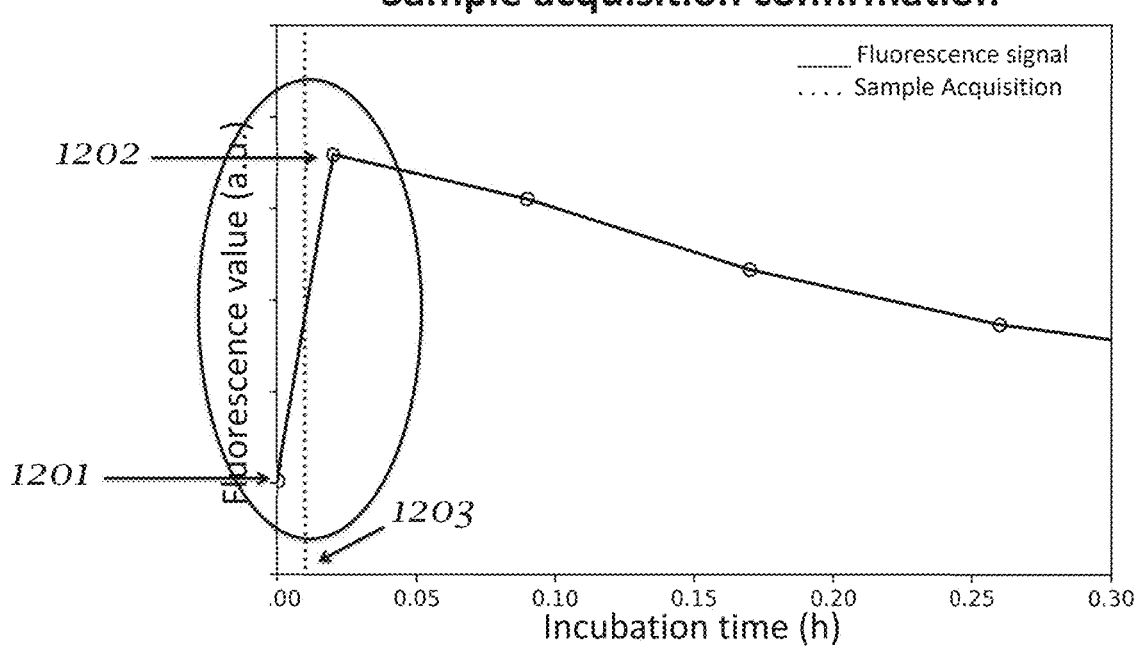
FIG. 12 is a graph that shows how an optical sensor may be used to detect the filling of the bottle, in order to provide sample assurance, in accordance with an embodiment of the invention.

Sample assurance: FIG. 12 is a graph that shows how an optical sensor may be used to detect the filling of the bottle, in order to provide sample assurance, in accordance with an embodiment of the invention. For example, the control electronics may perform one optical measurement (fluorescence, absorbance or both) prior to activating the sampling, and then again, after the moment when sampling is triggered. A difference between the two measurements represents confirmation that the optical properties of the bottle have changed, and thus provide proof that the sample was correctly acquired. An example of such optical sample assurance is given in FIG. 12, which shows the time evolution of the signal obtained from the fluorescence sensor. The first data point 1201 was measured prior to acquiring the sample, the second 1202 and subsequent points correspond to measurements performed after acquiring the sample 1203. As one can see on FIG. 12 (area highlighted by an oval), a difference in optical signal exists, which can then be used to confirm correct sample acquisition.

Instrument and Method for Quantifying Bacterial Contamination

In further embodiments of the invention, an apparatus is provided for measuring bacterial concentration. The apparatus may include, without limitation, a sampling device of the kinds described above, and represented graphically in FIGS. 1-7. Each sampling bottle as well as associated hardware may be, optionally, of a disposable single-use kind.

Each sample bottle may include a growth medium that enables bacterial growth. Such a growth medium may be specific to certain bacteria, or it may be a non-specific medium such as a simple glucose solution. Such reagent may come preloaded in each sampling bottle (for example, when the bottle is of disposable type) or may be manually introduced in each bottle during a maintenance operation prior to deploying the apparatus. The reagent may further include a chemical that can be used as an indicator of specific bacteria. For example, the reagent may include MUG or ONPG as described above, to detect presence of E. Coli and general Coliforms, respectively, or it may include ONPG2 for detecting enterococci, or other types of substances which may undergo observable changes in presence of bacteria. The reagent may include a combination of multiple such substances.

Each sampling bottle may be in contact with a temperature control apparatus outfitted with an optical sensor. Such temperature control apparatus enables the incubation of the sample/growth medium/reagent mixture at a temperature that allows growth of the bacteria of interest. Such temperature may be selected so as to preferentially allow the growth of certain types of bacteria or, alternatively, to inhibit the growth of other types of bacteria. For example, a higher incubation temperature may allow certain types of coliforms to preferentially develop (specifically the fecal coliforms).

Since such an apparatus performs a culture or incubation step which allows living bacterial to multiply, the measurement of bacterial concentration is not affected by dead cells present in the medium.

The optical sensor may be configured to repeatedly measure the optical properties of the sample/growth medium/ reagent mixture from the moment when the sample is acquired, and throughout the incubation period. A typical period for performing such measurements may be of the order of the second, of several seconds, of the minute, of several minutes, or of the hour. Such properties may include absorbance, fluorescence, turbidity, or other optical properties. The optical measurements may further be processed by the computing unit, which may also communicate them to a remote system, such as a computer or a server, for visualization and download. Such communication may be performed by any wired or wireless communication means known in the art. The apparatus or the remote server may produce automatic alerts and send them to an operator.

Each sampling bottle may have a filter at its inlet, in addition to the inlet check valve. Such a filter may have a pore size that allows dispersed bacteria to enter the sample bottle, but stops bacteria attached to particulate matter from entering the sample bottle. This would allow measurement of only the fully-dispersed bacteria (if the filter is used), or of total bacteria including those attached to particles (if no filter is used). The pore size will be adjusted depending on the characteristic size of the bacteria used, to ensure that all dispersed bacteria can pass through but limit as much as possible larger particles. A typical filter pore size that is effective for separating particulate from disperse E. Coli, for example, may be in the range from 2 μm to 5 μm.

Example: Method for Performing *E. Coli* and Total Coliform Measurements

In one instance, the apparatus for measuring the bacterial concentration is installed near a sensitive area requiring reinforced water quality monitoring for presence and quantification of *E. Coli* and total coliforms (TC). Such an area may be, but is not limited to: a recreational swimming spot, a drinking water inlet, an aquaculture zone, or a wastewater outflow.

The apparatus may be triggered to perform a bacterial measurement. Such a trigger may be a remote command received by the apparatus, or it could be an external sensor measurement falling outside its normal range. The sampling bottles in the apparatus contain a combination of growth medium, MUG and ONPG, as described above. Once the measurement trigger is received, the apparatus acquires a sample into one of the sample bottles. An optical sample assurance measurement is performed optically to confirm sample acquisition. The apparatus then starts incubating the sample/growth medium/reagent mixture at a temperature of 37 degrees Celsius, and performs repeated optical measurements of absorbance and fluorescence, so as to detect the appearance of MUF and ONP produced by the enzymatic activity of *E. Coli* and total coliforms, respectively. Absorbance could be measured, for example, at a wavelength of 430 nm, which corresponds to the absorbance peak of ONP, whereas fluorescence could be excited at a wavelength of 385 nm (allowing excitation of MUF fluorescence) and detected at a wavelength typically longer than 400 nm. An additional absorbance measurement could be performed at a wavelength where ONP or MUF do not absorb, for example at or around 610 nm. This optical measurement can then be used to quantify and correct for effects such as turbidity of the sample.

Figure 13:
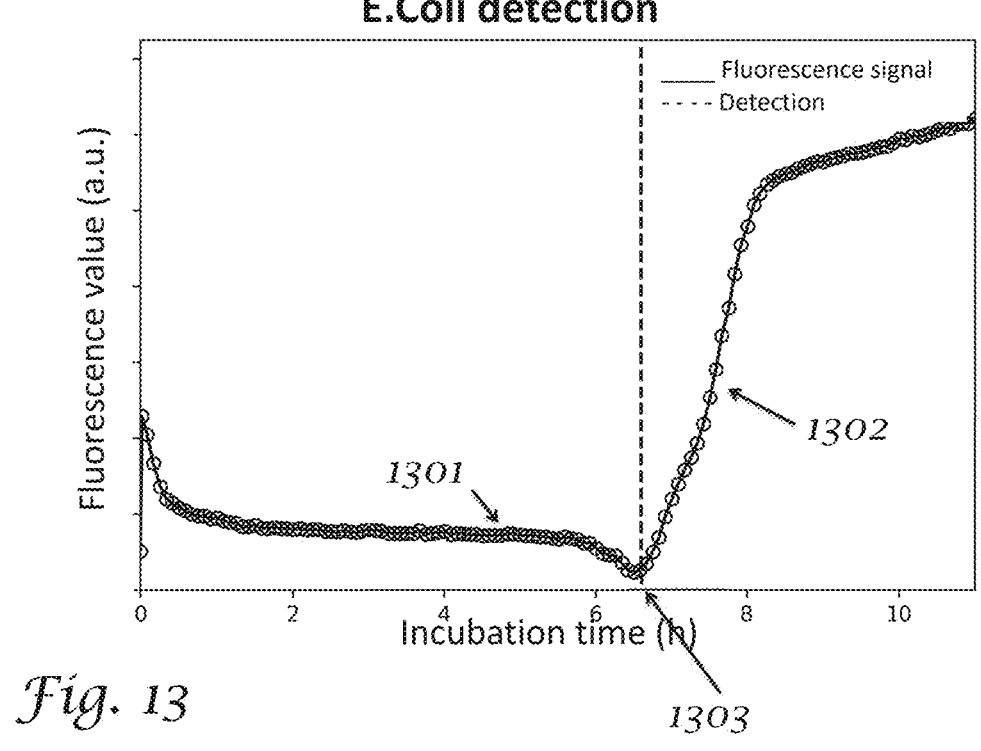
FIG. 13 shows a data curve of absorbance and fluorescence values measured throughout the incubation period, in accordance with various embodiments of the invention.
Figure 14:
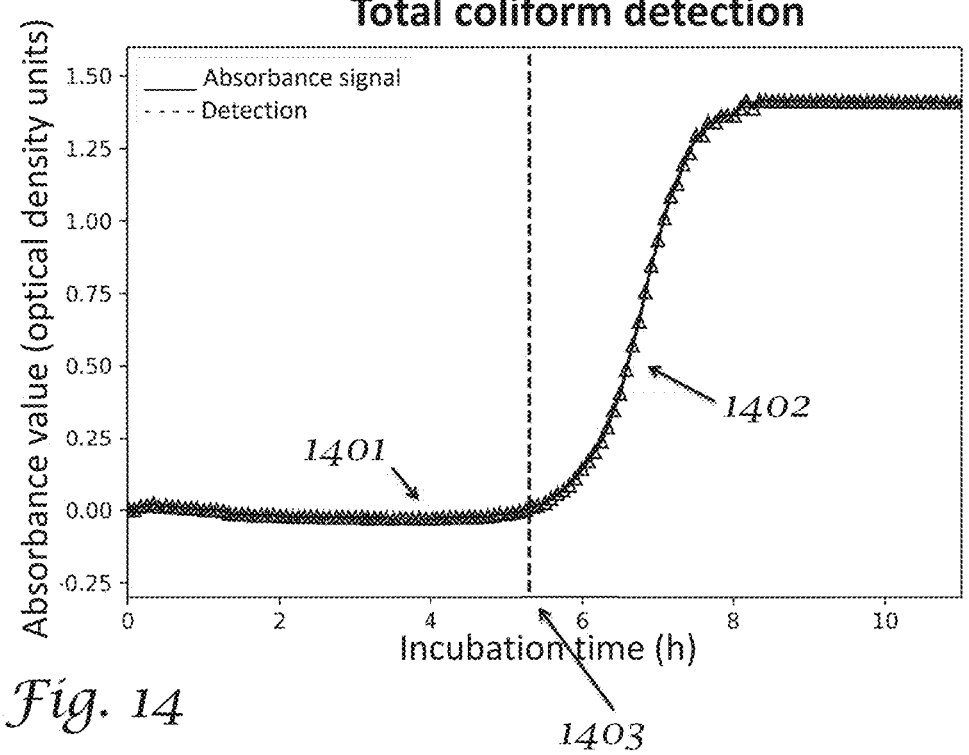
FIG. 14 shows another data curve of absorbance and fluorescence values measured throughout the incubation period, in accordance with various embodiments of the invention.

FIG. 13 shows a data curve of absorbance and fluorescence values measured throughout the incubation period, as does FIG. 14, in accordance with various embodiments of the invention. The values may be stored by the computing unit in internal memory, or transmitted to an external server, or both. The computing unit or the external server may process the data curves using an algorithm to determine the absorbance and fluorescence signal appearance times. Such data processing algorithm may consist of detecting the earliest point 1303, 1403 on the data curve after which the signal steadily increases (these detection points are marked by vertical lines in FIGS. 13 and 14, for the absorbance and fluorescence signals). Prior to such detection, the absorbance and fluorescence values are relatively stable (1301, 1401). Past the detection point, signals increase rapidly (1302, 1402). A person skilled in the art may recognize that many different types of algorithms can be used to detect the signal appearance times, and that the example given here is only one possibility.

Figure 15:
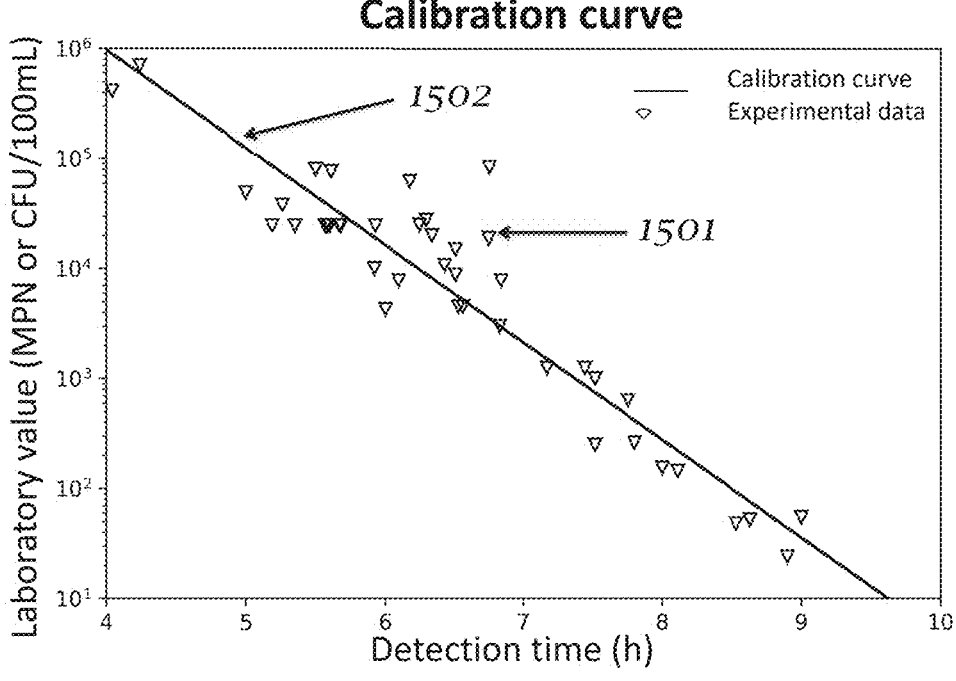
FIG. 15 is a graph that if multiple measurements, performed on samples of various bacterial concentrations, are plotted against the logarithm of the actual bacterial concentration in the original sample, measured with another reference technique, then a linear calibration can be obtained, in accordance with an embodiment of the invention.

Since living bacteria constantly multiply, the quantity of MUF and ONP produced increases rapidly. Past a certain threshold, the presence of these compounds can be readily detected by the optical sensor (see FIGS. 13 and 14). The culture or incubation time that is required prior to such detection (signal appearance times) depends on the initial number of living bacteria present in the sample, and therefore signal appearance times and initial bacterial (*E. Coli* and TC) concentrations are correlated. In particular, a shorter signal appearance time signifies higher bacterial concentrations in the initial sample. FIG. 15 shows that if multiple measurements 1501, performed on samples of various bacterial concentrations, are plotted against the logarithm of the actual bacterial concentration in the original sample, measured with another reference technique, then a linear calibration can be obtained (black line 1502), in accordance with an embodiment of the invention. This calibration may then be used in order to determine the actual concentration of bacteria initially present in the sample by measuring the signal appearance time (fluorescence appearance time in the case of *E. Coli* bacteria, represented in FIG. 15). Different calibrations may be obtained for different water matrices.

An advantage of the measurement technique presented above is that it is particularly robust, since it does not require extremely accurate optical measurements (absorbance or fluorescence). Since the measurement focuses on the time of signal appearance, and not on the actual values of the optical signal, the signal values do not have to be accurate, as long as their evolution over time is correctly captured. This has an important consequence for practical applications: while a change in the position of the sampling bottle from one measurement to the next may shift the overall values measured by the optical sensor, the shape of the curve and the corresponding detection time will remain unchanged and will therefore have no impact on the resulting bacterial quantification. Similarly, the amount of fluorescence or absorbance generated by different reagents may depend on other sample parameters such as pH, but their general time evolution may be unaffected thus not having a negative effect on the bacterial quantification.

This is an extremely important advantage compared to other rapid techniques whose measurement may depend on precise quantification of the amount of sample fluorescence or absorbance, the actual measurement value affecting the resulting bacterial quantification. For such methods, all sample parameters that can affect optical signal values need to be measured and/or controlled, which creates additional complications for implementation in an automatic instrument.

The computing unit or the remote server receiving the data throughout an incubation cycle may periodically apply the algorithm for detecting signal appearance times, and when a detection is made then it can use the stored calibration to calculate the bacterial concentration. The computing unit or remote server may then generate an automatic alert and transmit the result to an operator, by means of email, SMS, phone call, pop-up window or any other methods available for communication. If no detection can be made yet from the available data, the computing unit or remote server may provide an upper limit value, based on the quantification value corresponding to the current incubation time. Such upper limit may also be communicated to the operator.

The computing unit or the remote server may be connected to a graphical screen, or may provide a graphical interface over a network connection (such as a web site). On such a graphical interface, the operator may visualize the data, including the signal curves and the automatic detection times (as shown in FIGS. 13, 14). Furthermore, the operator may be allowed, upon inspection of the data, to validate or override the automatic detection provided by the computing unit or the remote server. The graphical interface may also be used to send control commands to the apparatus, so as to initiate a sample collection and analysis, or obtain operational data.

Device Employing Disposable Cartridges

It is further understood that the bottles and some or all of the associated hardware (any combination of adapters, inlet valves, flush valves, tubing, pumping filter, inlet filter, reagent, piston, bag, diaphragm) may be single-use components (disposable cartridges) that are installed prior to deployment and discarded after the samples are retrieved. The use of such single-use components can greatly simplify the logistics of operating a sampling and/or measurement device. By providing the sampling bottles as disposable cartridges, discarding them after the measurement is completed, and replacing with a new cartridge for a new deployment, the following advantages can be achieved:

The operator does not enter in direct contact with the previous samples, which may contain bacterial cultures and possibly high concentrations of pathogens, and therefore his safety is improved.

The new cartridges are already clean and free of contamination, so there is no need to perform additional cleaning and maintenance operations on the device. This speeds up the maintenance process and allows the unit to be serviced quickly directly in the field.

The cartridges may come prefilled with the chemical or biological reagent of interest, which eliminates the step of loading the reagent in the bottles prior to device deployment.

By providing cartridges that are quality controlled during the manufacturing process, the risk for human error in cleaning and preparing the device for a new deployment is minimized.

Figure 16:
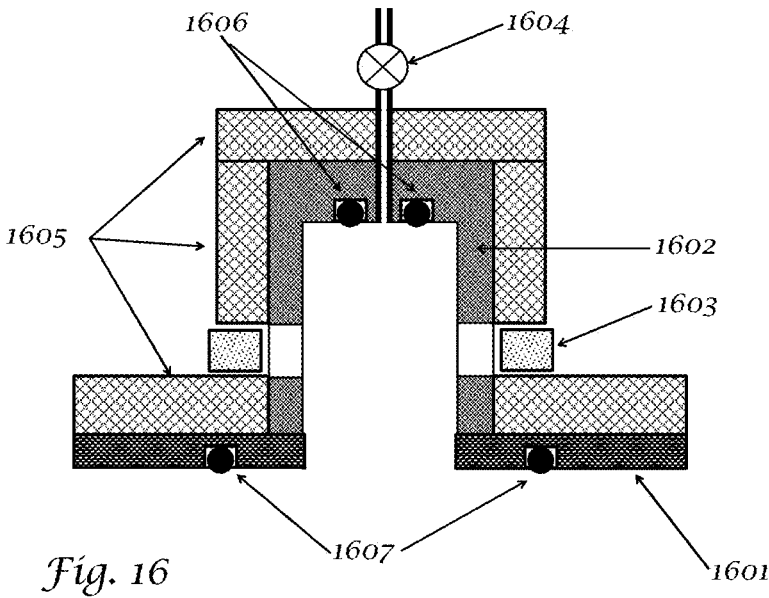
FIG. 16 shows an exemplary sample analysis device made for using disposable cartridges, in accordance with an embodiment of the invention.

FIG. 16 shows an exemplary sample analysis device made for using disposable cartridges, in accordance with an embodiment of the invention. The exemplary device may include, attached to the device external wall 1601, a bioreactor containing the temperature control apparatus 1602 and optical sensor 1603. The temperature control apparatus and the device wall may be isolated using a thermally isolating material 1605. The bioreactor may be connected, via a control valve 1604, to the devices' pump (not shown). Water- and/or air-proof sealing elements 1606 and 1607 may also be included, and may consist of gaskets, o-rings of various cross-sections, or any other type of sealing solution known in the art.

Figure 17:
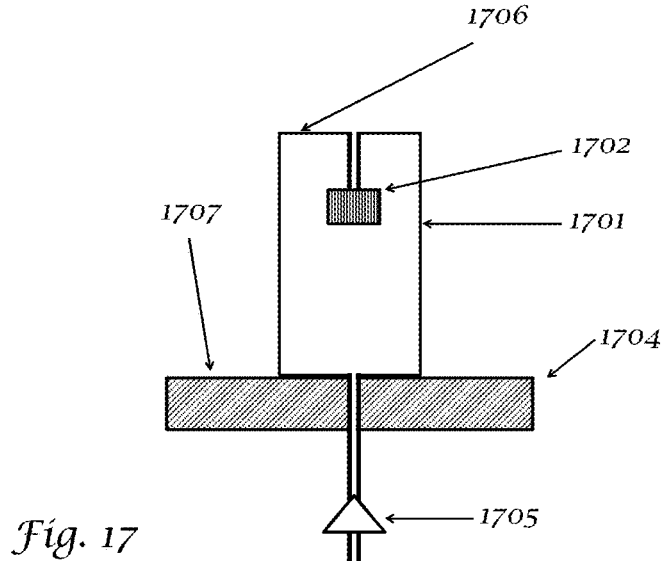
FIG. 17 shows a disposable cartridge that could be used with the device of FIG. 16, in accordance with an embodiment of the invention.
Figure 18:
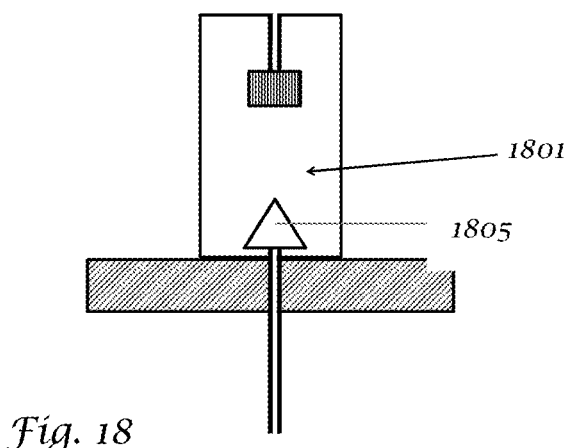
FIG. 18 shows an alternate position of the inlet check valve, inside the bottle of the disposable cartridge, in accordance with an embodiment of the invention.

FIG. 17 shows a disposable cartridge that could be used with the device of FIG. 16, in accordance with an embodiment of the invention. The disposable cartridge may include a sample bottle 1701 that is attached to a bottle support plate 1704. Alternatively, the two may be manufactured as one part. The bottle 1701 further includes, or is attached to, an inlet check valve 1705 as well as a pumping filter 1702, in any of the configurations previously taught in this invention. The cartridge further may include sealing surfaces 1706 and 1707, which are designed to mate with seals 1606 and 1607 on the sample analysis device. FIG. 18 shows an alternate position of the inlet check valve 1805, inside the bottle 1801 of the disposable cartridge, in accordance with an embodiment of the invention. The person skilled in the art will understand that a multitude of configurations are possible for the positioning of the different elements described here, and the examples taught are only some possible embodiments.

Figure 19:
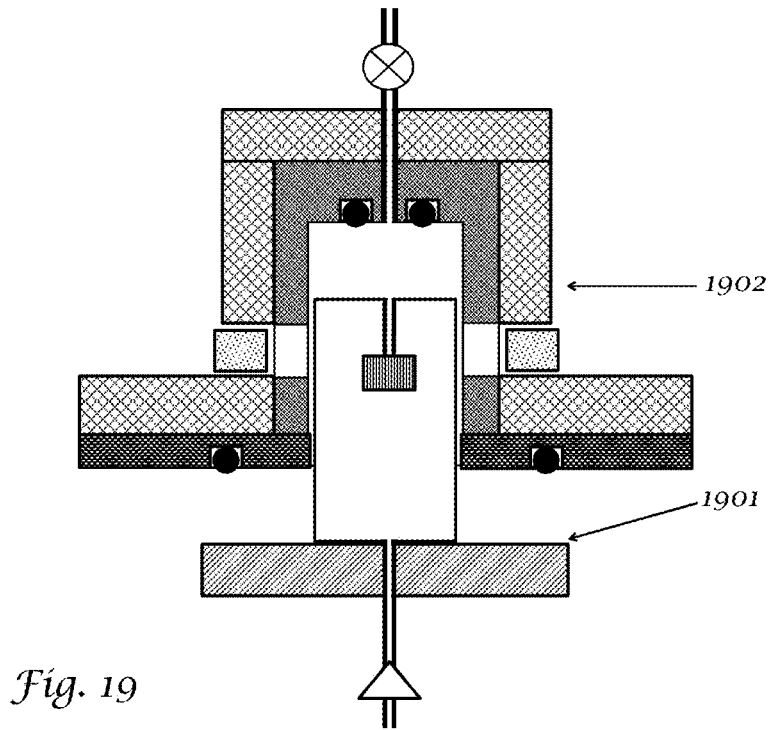
FIG. 19 shows a disposable cartridge 1901 being inserted into a device bioreactor, in accordance with an embodiment of the invention.
Figure 20:
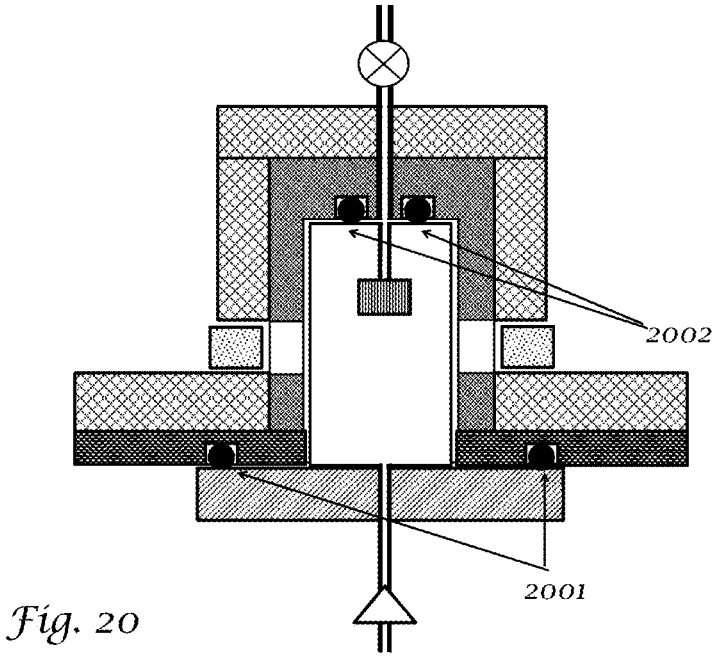
FIG. 20 shows a disposable cartridge mating with a device bioreactor with sealing elements engaged, in accordance with an embodiment of the invention.
Figure 21:
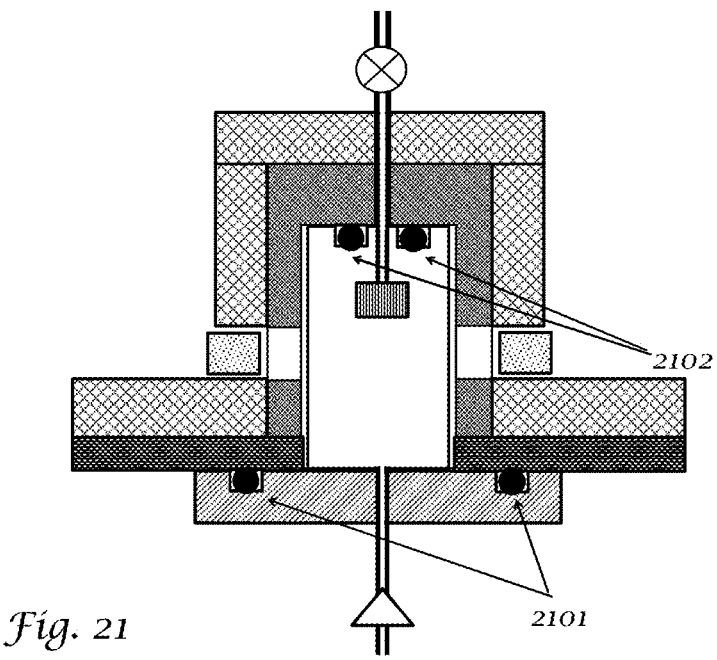
FIG. 21 shows a seal configuration as part of the disposable cartridge, in accordance with an embodiment of the invention.
Figure 22:
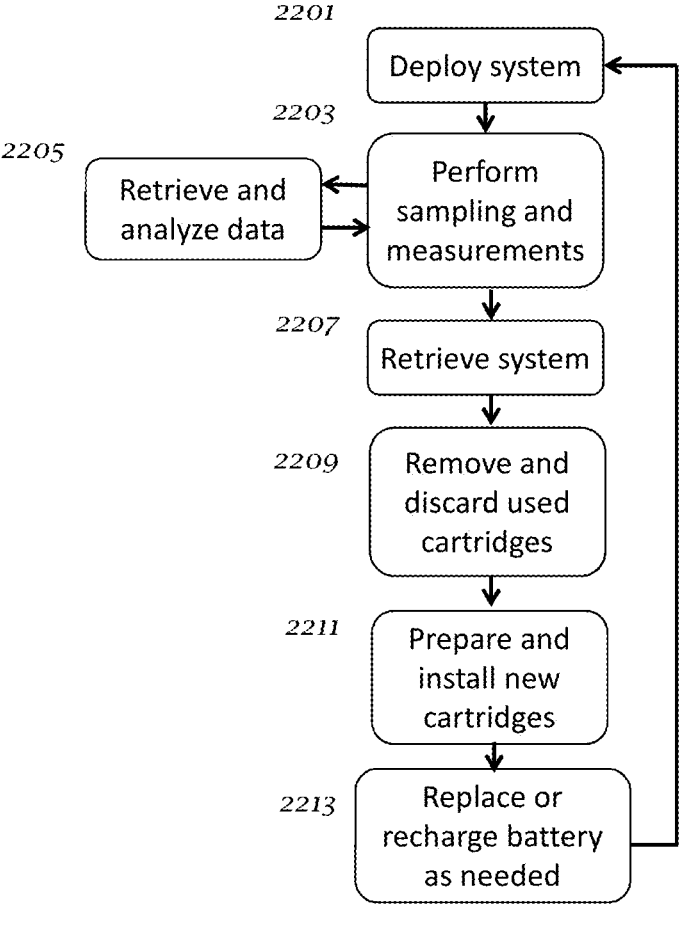
FIG. 22 shows a schematic flowchart describing the usage of a sample analysis device made for using disposable cartridges, in accordance with an embodiment of the invention.

FIG. 19 shows the disposable cartridge 1901 being inserted into the device bioreactor 1902, in accordance with an embodiment of the invention. FIG. 20 shows the disposable cartridge mating with the device bioreactor with the sealing elements engaged (2001, 2002), in accordance with an embodiment of the invention. FIG. 21 shows another seal configuration, with sealing elements 2101, 2012 as part of the disposable cartridge, in accordance with an embodiment of the invention.

Figure 23:
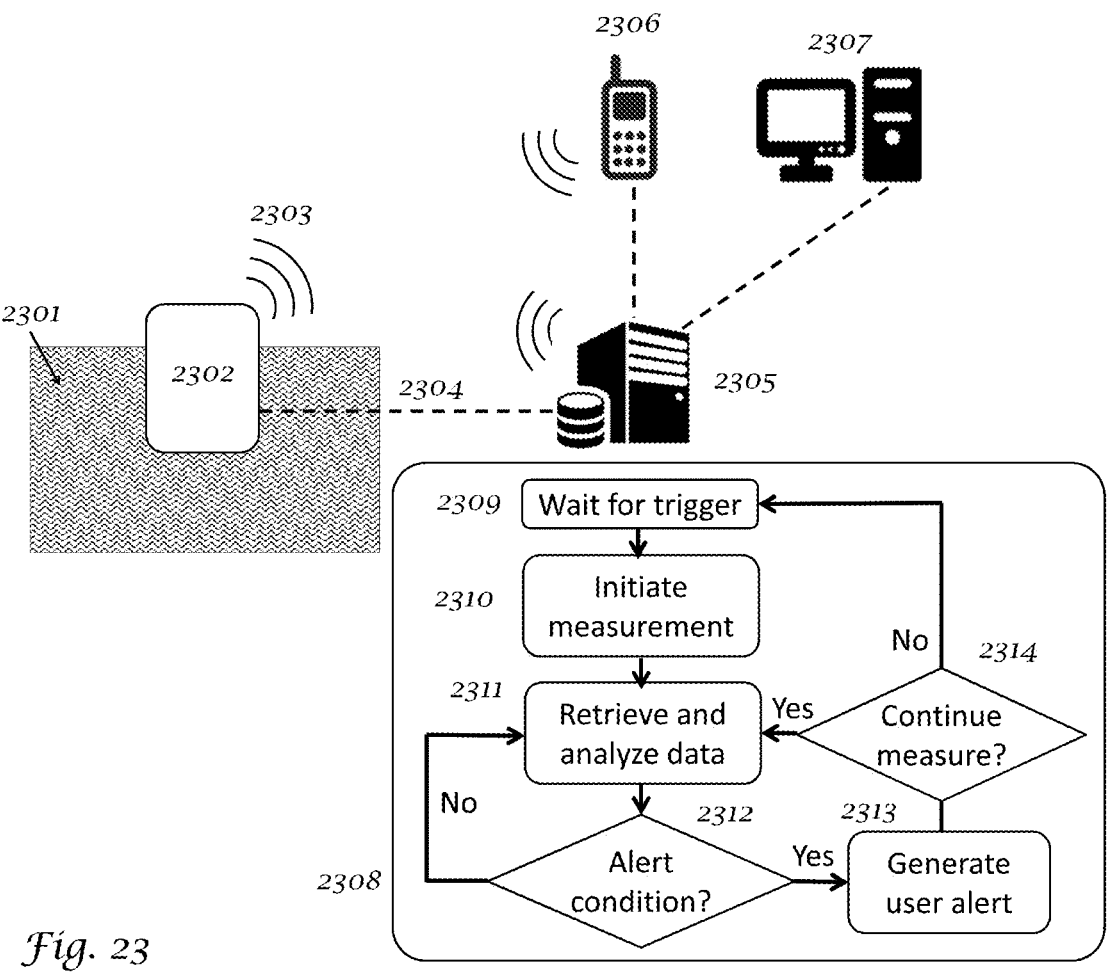
FIG. 23 shows a schematic diagram of a system for bacterial monitoring of a site, including a sample analysis device, and further including a server or cell phone with which said device can communicate, means to visualize and analyze the data transmitted by the device, and means of generating an alert when certain conditions are satisfied by the data from the device, in accordance with an embodiment of the invention.

FIG. 23 shows schematically the components of a system for performing bacterial monitoring of an aquatic site 2301. The system includes one or multiple sample analysis devices 2302, such as described above, which are further capable of wireless 2303 or wired 2304 bidirectional communication with a server 2305 and/or a cell phone 2306. The server 2305 may be accessible from a user computer terminal 2307, through a computer network. The server 2305 may optionally be capable to communicate directly with the cell phone 2306. The system may be configured to perform a process 2308, which may use data provided by the sample analysis devices 2302, and from other sources such as (without any limitation) a clock, a separate sensor, a control center, cell phone 2306 or computer terminal 2307, a user interface or an operator-generated command, and based on the received data, may wait until a trigger condition is met, step 2309, at which time it can initiate a sampling and measurement event, step 2310, by one or several of the sample analysis devices 2302. The process 2308 will then, step 2311, use and analyze data retrieved from the device 2302, and checks whether an alert condition is met, step 2312. If such condition is not met, the process 2308 returns to step 2311 and continues retrieving data and checking. If the alert condition is met, the process 2308 generates a user alert, step 2313, which may be communicated through the cell phone 2306, the computer terminal 2307, or by any other communication means. The process 2308 then decides whether to continue the measurement, step 2314. If the measurement needs to be continued, it returns to step 2311 and continues retrieving data and checking for the alert condition. If the measurement is to be stopped, the process 2308 returns to step 2309. It is understood that process 2308 may be implemented directly within the controller of the device 2302, within server 2305, within cell phone 2306, within the user computer terminal 2307, or within a separate controller or computing unit. Furthermore, the process may be implemented in hardware, software, or a combination thereof.

The person skilled in the art will recognize that the examples above are only some of many possible ways to use the invention described here. For example, the use of disposable cartridges is also possible for other type of applications than bacterial detection. Such application examples could be sample collection, or performing chemical measurements.

Other species of bacteria could be measured using the methods taught herein, using different types of selective reagents, varying incubation temperatures, or different wavelengths for optical interrogation. Any of the variants of sampling devices described herein could be used in conjunction with this bacterial measurement method; allowing similar bacterial measurements to be performed in a multitude of locations, such as: on water coming from a pipe, from surface or from different depths in a natural environment, or even from deep water in the ocean or sea.

Embodiments of the invention, for example and without limitation, portions of the controller, portions of the control electronics, portions of the temperature control apparatus, and/or portions of any analysis module utilized, may be implemented in whole or in part in any conventional computer programming language. For example, preferred embodiments may be implemented in assembly language, a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system (for example, the controller). Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL.)

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A system for quantifying contamination of a fluidic sample by a type of bacteria of interest, the system comprising:
   a sample bottle into which a sample fluid is acquired;
   a reagent providing an optical signature in presence of the bacteria of interest, that is mixed with the sample fluid;
   an optical sensor for obtaining a fluorescence optical signal and/or an absorbance optical signal from the sample fluid at multiple times, said optical sensor using a minimum of two wavelengths for measuring the absorbance optical signal, whereas the two wavelengths are selected such that one is more sensitive than the other to the optical signature of the reagent, said optical sensor including light sources and a light detector;
   a temperature controller apparatus for incubating the sample fluid, the temperature controller apparatus positioned around the sample bottle and including openings; and

a controller configured to determine bacterial concentration of the sample fluid as a function of a shape of a fluorescence versus time curve and/or an absorbance versus time curve obtained from the at least one optical sensor during incubation of the fluidic sample,
   wherein the optical sensor is positioned around the temperature controller apparatus, the light sources and the light detector being aligned with the openings of the temperature controller apparatus.

2. The system according to claim 1, wherein the controller is configured to compare the fluorescence and/or absorbance signal appearance times with a calibration curve, the calibration curve based, at least in part, on comparing signal appearance times of a plurality of sample fluids obtained previously with their actual bacterial concentrations determined using another reference technique.

3. The system according to claim 1, wherein the sample bottle includes a growth medium that enables the growth of the bacteria of interest.

4. The system according to claim 1, further containing multiple sample bottles, each bottle used to measure a single fluid sample, the system being able to perform multiple measurements in parallel.

5. The system according to claim 1, wherein the system is portable and/or submersible, and configured to operate on battery and transmit data wirelessly.

6. The system according to claim 1, wherein the optical sensor has the shape of a sensor ring.

7. The system according to claim 1, wherein the optical sensor is positioned at a midway height of the sample fluid in the sample bottle.

8. A method of quantifying contamination of a fluidic sample by a type of bacteria of interest, the method comprising:
   acquiring a sample fluid in a sample bottle;
   mixing the sample fluid with a reagent providing an optical signature in presence of the bacteria of interest;
   measuring at multiple times, using an optical sensor, a fluorescence optical signal and/or an absorbance optical signal from the sample fluid, whereas a minimum of two wavelengths of light are used to measure the absorbance signal, the two wavelengths being selected such that one is more sensitive than the other to the optical signature of the reagent, said optical sensor including light sources and a light detector;
   incubating the sample fluid prior to, or during the measuring using a temperature controller apparatus;
   determining bacterial concentration of the sample fluid as a function of a shape of a fluorescence versus time curve and/or an absorbance versus time curve obtained from the at least one optical sensor during incubation of the fluidic sample,
   wherein the temperature controller apparatus is positioned around the sample bottle and includes openings, and the optical sensor is positioned around the temperature controller apparatus, the light sources and the light detector being aligned with the openings of the temperature controller apparatus.

9. The method according to claim 8, wherein determining includes comparing the fluorescence and/or absorbance signal appearance times with a calibration curve, the calibration curve based, at least in part, on comparing signal appearance times of a plurality of sample fluids obtained previously with their actual bacterial concentrations determined using another reference technique.

10. The method according to claim 8, wherein the sample bottle includes a growth medium that enables bacterial growth.

11. The method according to claim 8, further including analyzing multiple samples in separate bottles, successively or in parallel.

12. The method according to claim 8, wherein the optical sensor has the shape of a sensor ring.

13. The method according to claim 8, the optical sensor is positioned at a midway height of the sample fluid in the sample bottle.

\* \* \* \* \*